US008110193B2

(12) United States Patent
Zeng

(10) Patent No.: US 8,110,193 B2
(45) Date of Patent: Feb. 7, 2012

(54) METHODS FOR CONDITIONING A SUBJECT FOR HEMATOPOIETIC CELL TRANSPLANTATION

(75) Inventor: Defu Zeng, Arcadia, CA (US)

(73) Assignee: City of Hope, Duarte, CA (US)

( * ) Notice: Subject to any disclaimer, the term of this patent is extended or adjusted under 35 U.S.C. 154(b) by 340 days.

(21) Appl. No.: 12/338,763

(22) Filed: Dec. 18, 2008

(65) Prior Publication Data

US 2009/0162370 A1 Jun. 25, 2009

Related U.S. Application Data

(60) Provisional application No. 61/016,436, filed on Dec. 21, 2007.

(51) Int. Cl.
*A61K 39/395* (2006.01)
(52) U.S. Cl. .................................. 424/154.1; 424/144.1
(58) Field of Classification Search .................... None
See application file for complete search history.

(56) References Cited

U.S. PATENT DOCUMENTS

| 5,583,002 | A  | 12/1996 | Ochoa et al. |
| 5,762,927 | A  | 6/1998  | Knechtle et al. |
| 5,767,072 | A  | 6/1998  | Vitetta et al. |
| 6,103,235 | A  | 8/2000  | Neville et al. |
| 7,186,697 | B2 | 3/2007  | Marasco et al. |
| 2002/0182727 | A1 | 12/2002 | Freeman et al. |
| 2005/0238626 | A1 | 10/2005 | Yang et al. |
| 2010/0249039 | A1 | 9/2010  | Zangemeister-Wittke et al. |

OTHER PUBLICATIONS

Ringden et al., Transplantation. vol. 66(5), Sep. 15, 1998, pp. 620-625.*
Marks et al., Expert Opin Investig Drugs. Dec. 2005;14(12):1497-511.*
Ziwei Huang, Pharmacol Ther. Jun. 2000;86(3):201-15.*
Li et al., Blood, Nov. 16, 2007, vol. 110, No. 11, Part 1, pp. 645A.*
Alegre, M., et al., "Hypothennia and Hypoglycemia Induced by Anti-CD3 Monoclonal Antibody in Mice: Role of Tumor Necrosis Factor," Eur J Immunol 20:707-710 (1990).
Chakraverty, R., et al., "An Inflammatory Checkpoint Regulates Recruitment of Graft-Versus-Host Reactive T Cells to Peripheral Tissues," J Exp Med 203:2021-2031 (2006).
Leng, C., et al., "Reduction of Graft-Versus-Host Disease by Histone Deacetylase Inhibitor Suberonylanilide Hydroxamic Acid is Associated with Modulation of Inflammatory Cytokine Milieu and Involves Inhibition of STAT1," Exp Hematol 34:776-87 (2006).
Leoni, F., et al., "The Antitumor Histone Deacetylase Inhibitor Suberoylanilide Hydroxamic Acid Exhibits Antiinflammatory Properties Via Suppression of Cytokines," Proc Natl Acad Sci USA 99:2995-3000 (2002).
Zhang, C., et al., "Elimination of Insulitis and Augmentation of Islet Cell Regeneration Via Induction of Chimerism in Overtly Diabetic NOD Mice," Proc Natl Acad Sci USA 104:2337-2342 (2007).

Agata, Y., et al., "Expression of the PD-1 Antigen on the Surface of Stimulated Mouse T and B Lymphocytes," Int. Immunol. 8:765-772 (1996).
Liang, Y., et al., "Donor CD8+ T Cells Facilitate Induction of Chimerism and Tolerance Without GVHD in Autoimmune NOD Mice Conditioned With Anti-CD3 mAb," Blood 105:2180-2188 (2005).
Marks, P., et al., "Histone Deacetylases and Cancer: Causes and Therapies," Nat Rev Cancer 1:194-202 (2001).
Marks, P.A., et al., "Histone Deacetylases," Curr Opin Pharmacol 3:344-51 (2003).
Mishra, N., et al., "Histone Deacetylase Inhibitors Modulate Renal Disease in the MRL-Ipr/Ipr Mouse," J Clin Invest 111:539-552 (2003).
Morris, E.S., et al., "NKT Cell—Dependent Leukemia Eradication Following Stem Cell Mobilization With Potent G-CSF Analogs," J Clin Invest 115:3093-3103 (2005).
Reddy, P. et al., "Histone Deacetylase Inhibitor Suberoylanilide Hydroxamic Acid Reduces Acute Graft-Versus-Host Disease and Preserves Graft-Versus-Leukemia Effect," Proc Natl Acad Sci USA 101:3921-3926 (2004).
Roth, S. Y., et al., "Histone Acetyltransferases," Annu Rev Biochem 70:81-120 (2001).
Shlomchik, W.D., et al., "Prevention of Graft Versus Host Disease by Inactivation of Host Antigen-Presenting Cells," Science 285:412-415 (1999).
Smith-Berdan, S., et al., "Reversal of Autoimmune Disease in Lupus-Prone New Zealand Black/New Zealand White Mice by Nonmyeloablative Transplantation of Purified Allogeneic Hematopoietic Stem Cells," Blood 110:1370-1378 (2007).
Sykes, M., et al., "Treatment of Severe Autoimmune Disease by Stem-Cell Transplantation," Nature 435:620-627 (2005).
Teshima, T., et al., "Acute Graft-Versus-Host Disease Does Not Require Alloantigen Expression on Host Epithelium," Nat Med 8:575-581 (2002).
Xu, W.S., et al., "Histone Deacetylase Inhibitors: Molecular Mechanisms of Action," Oncogene 26:5541-52 (2007).
Zeng, D., et al., "Cutting Edge: A Role for CD1 in the Pathogenesis of Lupus in NZB/NZW Mice," J Immunol 164:5000-5004 (2000).
Zeng, D., et al., "Activation of Natural Killer T Cells in NZB/W Mice Induces Th1-type Immune Responses Exacerbating Lupus," J Clin Invest 112:1211-1222 (2003).
Zhang, C., et al., "Donor CD8 T Cells Mediate Graft-versus-Leukemia Activity without Clinical Signs of Graft-versus-Host Disease in Recipients Conditioned with Anti-CD3 Monoclonal Antibody," J Immunol 178:838-850 (2007).

(Continued)

*Primary Examiner* — Zachary Skelding
(74) *Attorney, Agent, or Firm* — Perkins Coie LLP; Patrick D. Morris

(57) ABSTRACT

Allogeneic hematopoietic cell transplantation (HCT) is an effective therapy for treatment of hematological malignancies and various autoimmune conditions. However, HCT traditionally requires conditioning by total body irradiation and/or chemotherapy, both of which are toxic and induce GVHD. Provided herein are compositions and methods for conditioning a subject for HCT by administering one or more anti-CD3 compounds and one or more histone deacetylase inhibitors. Also provided herein are methods for reducing GVHD in a subject receiving total body irradiation prior to HCT comprising administering one or more anti-CD3 compounds to the subject prior to total body irradiation.

3 Claims, 11 Drawing Sheets

OTHER PUBLICATIONS

Alegre, M.L., et al., "Cytokine Release Syndrome Induced by the 145-2C11 Anti-CD3 Monoclonal Antibody in Mice: Prevention by High Doses of Methylpresdnisolone," J. Immunol. 146(4): 1184-1191 (1991).

Annunziato, F., et al., "Assessment of Chemokine Receptor Expression by Human Th1 and Th2 Cells In Vitro and In Vivo," J. Leukoc. Biol. 65:691-699 (1999).

Appelbaum, F. R., "Haematopoietic Cell Transplantation as Immunotherapy," Nature 411:385-389 (2001).

Atkinson, M.A., et al., "The NOD Mouse Model of Type 1 Diabetes: As Good As It Gets?" Nat. Med. 5:601-604 (1999).

Baker, J., et al., "Expansion of Cytolytic CD8+ Natural Killer T Cells with Limited Capacity for Graft-Versus-Host Disease Induction Due to Interferon Gamma Production," Blood 97:2923-2931 (2001).

Beaty, S. R., et al., "Diverse and Potent Chemokine Production by Lung CD11b$^{high}$ Dendritic Cells in Homeostasis and in Allergic Lung Inflammation," J. Immunol. 178:1882-1895 (2007).

Beilhack, A., et al., "In Vivo Analyses of Early Events in Acute Graft-Versus-Host Disease Reveal Sequential Infiltration of T-Cell Subsets," Blood 106:1113-1122 (2005).

Beilhack, A., et al., "Prevention of Acute Graft-Versus-Host Disease by Blocking T-Cell Entry to Secondary Lymphoid Organs," Blood 111:2919-2928 (2008).

Beilhack, G.F., et al., "Purified Allogeneic Hematopoietic Stem Cell Transplantation Blocks Diabetes Pathogenesis in NOD Mice," Diabetes 52:59-68 (2003).

Belghith, M., et al., "TGF-Beta-Dependent Mechanisms Mediate Restoration of Self-Tolerance Induced by Antibodies to CD3 in Overt Autoimmune Diabetes," Nat. Med. 9:1202-1208 (2003).

Blazar, B.R., et al., "In Vivo or In Vitro Anti-CD3 Epsilon Chain Monoclonal Antibody Therapy for the Prevention of Lethal Murine Graft-Versus-Host Disease Across the Major Histocompatibility Barrier in Mice[1]," J. Immunol. 152:3665-3674 (1994).

Blazar, B. R., et al., "Anti-CD3εF(ab')$_2$ Fragments Inhibit T Cell Expansion in Vivo During Graft-Versus-Host Disease or the Primary Immune Response to Nominal Antigen," J. Immunol. 159:5821-5833 (1997).

Blazar, B. R., et al., "Blockade of Programmed Death-1 Engagement Accelerates Graft-Versus-Host Disease Lethality by an IFN-γ-Dependent Mechanism," J. Immunol. 171:1272-1277 (2003).

Bluestone, J.A., et al., "Natural Versus Adaptive Regulatory T Cells," Nat. Rev. Immunol. 3:253-257 (2003).

Burman, A. C., et al., "IFN{gamma} Differentially Controls the Development of Idiopathic Pneumonia Syndrome and GVHD of the Gastrointestinal Tract," Blood 110:1064-1072 (2007).

Burt, R.K., et al., "Hematopoietic Stem Cell Therapy of Autoimmune Diseases," Curr. Opin. Hematol. 5:472-477 (1998).

Campbell, D.J., et al., "Targeting T Cell Responses by Selective Chemokine Receptor Expression," Semin. Immunol. 15:277-286 (2003).

Cao, Y.A., et al., "Shifting Foci of Hematopoiesis During Reconstitution from Single Stem Cells," PNAS 101:221-226 (2004).

Castano, L., et al., "Type-I Diabetes: A Chronic Autoimmune Disease of Human, Mouse, and Rat," Annu. Rev. Immunol. 8:647-679 (1990).

Chakraverty, R., et al., "The Role of Antigen-Presenting Cells in Triggering Graft-Versus-Host Disease and Graft-Versus-Leukemia," Blood 110:9-17 (2007).

Chatenoud, L., et al., "CD3 Antibody-Induced Dominant Self Tolerance in Overtly Diabetic NOD Mice[1]," J. Immunol. 158:2947-2954 (1997).

Chatenoud, L., et al., "CD3-Specific Antibodies: A Portal to the Treatment of Autoimmunity," Nat. Rev. Immunol. 7:622-632 (2007).

Chen, L., "Co-Inhibitory Molecules of the B7-CD28 Family in the Control of T-Cell Immunity," Nat. Rev. Immunol. 4:336-347 (2004).

Cooke, K. R., et al., "An Experimental Model of Idiopathic Pneumonia Syndrome After Bone Marrow Transplantation: I. The Roles of Minor H Antigens and Endotoxin," Blood 88:3230-3239 (1996).

Cooke, K. R., et al., "LPS Antagonism Reduces Graft-Versus-Host Disease and Preserves Graft-Versus-Leukemia Activity After Experimental Bone Marrow Transplantation," J. Clin. Invest. 107:1581-1589 (2001).

Cooke, K.R., et al., "A Protective Gene for Graft-Versus-Host Disease," N. Engl. J. Med. 349:2183-2184 (2003).

Coombes, J. L., et al., "A Functionally Specialized Population of Mucosal CD103$^+$DCs Induces Foxp3$^+$Regulatory T Cells Via a TGF-β- and Retinoic Acid-Dependent Mechanism," J. Exp. Med. 8:1757-1764 (2007).

Decalf, J., et al., "Plasmacytoid Dendritic Cells Initiate a Complex Chemokine and Cytokine Network and are a Viable Drug Target in Chronic HCV Patients," J. Exp. Med. 204:2423-2437 (2007).

Dong, H., et al., "B7-H1 Determines Accumulation and Deletion of Intrahepatic CD8$^+$T Lymphocytes," Immunity 20:327-336 (2004).

Dong, H., et al., "Tumor-Associated B7-H1 Promotes T-Cell Apoptosis: A Potential Mechanism of Immune Evasion," Nat. Med. 8:793-800 (2002).

Dor, Y., et al., "Adult Pancreatic Beta-Cells are Formed by Self-Duplication Rather Than Stem-Cell Differentiation," Nature 429:41-46 (2004).

Drakes, M. L., et al., "Isolation and Purification of Colon Lamina Propria Dendritic Cells from Mice with Colitis," Cytotechnology 46:151-161 (2004).

Duffner, U. A., et al., "Host Dendritic Cells Alone are Sufficient to Initiate Acute Graft-Versus-Host Disease," J. Immunol. 172:7393-7398 (2004).

Duffner, U., et al., "Role of CXCR3-Induced Donor T-Cell Migration in Acute GVHD," Exp. Hematol. 31:897-902 (2003).

Exner, B.G., et al., "Bone Marrow Transplantation for Therapy in Autoimmune Disease," Stem Cells 15(suppl 1):171-175 (1997).

Ferrara, J.L., "Pathogenesis of Acute Graft-Versus-Host Disease: Cytokines and Cellular Effectors," J. Hematother. Stem Cell Res. 9:299-306 (2000).

Ferrara, J., et al., "The Pathophysiology of Graft-vs-Host Disease," Hematopoietic Cell Transplantation. Malden: Blackwell Science Ltd. 353-368 (2004).

Fife, B. T., et al., "Control of Peripheral T-Cell Tolerance and Autoimmunity Via the CTLA-4 and PD-1 Pathways," Immunol. Rev. 224:166-182 (2008).

Gandy, K.L., et al., "CD8$^+$TCR$^+$ and CD8$^+$TCR$^-$ Cells in Whole Bone Marrow Facilitate the Engraftment of Hematopoietic Stem Cells Across Allogeneic Barriers," Immunity 11:579-590 (1999).

Giralt, S., "Reduced-Intensity Conditioning Regimens for Hematologic Malignancies: What Have We Learned Over the Last 10 Years?" Hematology Am. Soc. Hematol. Educ. Program 384-389 (2005).

Gonzalez, M., et al., "The Balance Between Donor T Cell Anergy and Suppression Versus Lethal Graft-Versus-Host Disease is Determined by Host Conditioning[1]," J. Immunol. 169:5581-5589 (2002).

Goudy, K.S., et al., "Systemic Overexpression of IL-10 Induces CD4$^+$CD25$^+$Cell Populations In Vivo and Ameliorates Type 1 Diabetes in Nonobese Diabetic Mice in a Dose-Dependent Fashion[1]," J. Immunol. 171:2270-2278 (2003).

Greenwald, R. J., et al., "The B7 Family Revisited," Annu. Rev. Immunol. 23:515-548 (2005).

Hancock, W.W., et al., Requirement of the Chemokine Receptor CXCR3 for Acute Allograft Rejection. J. Exp. Med. 192:1515-1519 (2000).

Hancock, W.W., et al., "Donor-Derived IP-10 Initiates Development of Acute Allograft Rejection," J. Exp. Med. 193:975-980 (2001).

Haspot, F., et al., "Peripheral Deletional Tolerance of Alloreactive CD8 But Not CD4 T Cells is Dependent on the PD-1/PD-L1 Pathway," Blood 112:2149-2155 (2008).

Herold, K.C., et al., "Anti-CD3 Monoclonal Antibody in New-Onset Type 1 Diabetes Mellitus," N. Engl. J. Med. 346:1692-1698 (2002).

Hieshima, K., et al., CC CHemokine Ligands 25 and 28 Play Essential Roles in Intestinal Extravasation of IfA Antibody-Secreting Cells, J. Immunol. 173:3668-3675 (2004).

Hildebrandt, G. C., et al., "Blockade of CXCR3 Receptor: Ligand Interactions Reduces Leukocyte Recruitment to the Lung and the Severity of Experimental Idiopathic Pneumonia Syndrome," J. Immunol. 173:2050-2059 (2004).

Hill, G.R., et al., "Total Body Irradiation and Acute Graft-Versus-Host Disease: the Role of Gastrointestinal Damage and Inflammatory Cytokines," Blood 90:3204-3213 (1997).

Ianus, A., et al., "In Vivo Derivation of Glucose-Competent Pancreatic Endocrine Cells from Bone Marrow Without Evidence of Cell Fusion," J. Clin. Invest. 111:843-850 (2003).

Iishida, M., et al., "Differential Expression of PD-L1 and PD-L2, Ligands for an Inhibitory Receptor PD-1, in the Cells of Lymphohematopoietic Tissues," Immunol. Lett. 84:57-62 (2002).

Itabashi, Y., et al., "Allogeneic Chimerism Established with a Mixture of Low Dose Bone Marrow Cells and Splenocytes in Sublethally Irradiated Mice," Transplant Immunology 10:25-30 (2002).

Iwata, M., et al., "Retinoic Acid Imprints Gut-Homing Specificity on T Cells," Immunity 21:527-538 (2004).

Jaksch, M., et al., "Increased Gene Expression of Chemokine Receptors is Correlated with Acute Graft-Versus-Host Disease After Allogeneic Stem Cell Transplantation," Biol. Blood Marrow Transplant. 11:280-287 (2005).

Johansson-Lindbom, B., et al., "Functional Specialization of Gut $CD103^+$ Dendritic Cells in the Regulation of Tissue-Selective T cell Homing," J. Exp. Med. 202:1063-1073 (2005).

Johansson-Lindbom, B., et al., "Selective Generation of Gut Tropic T Cells in Gut-Associated Lymphoid Tissue (GALT): Requirement for GALT Dendritic Cells and Adjuvant," J. Exp. Med. 198:963-969 (2003).

Johnson, B. D., et al., "Use of Anti-CD3ε $F(ab')_2$ Fragments In Vivio to Modulate Graft-Versus-Host Disease Without Loss of Graft-Versus-Leukemia Reactivity After MHC-Matched Bone Marrow Transplantation," J. Immunol. 154:5542-5554 (1995).

Kaplan, D. H., et al., "Target Antigens Determine Graft-Versus-Host Disease Phenotype," J. Immunol. 173:5467-5475 (2004).

Kaufman, C.L., et al., "Patterns of Hemopoietic Reconstitution in Nonobese Diabetic Mice: Dichotomy of Allogeneic Resistance Versus Competitive Advantage of Disease-Resistant Marrow[1]," Immunol 158:2435-2442 (1997).

Keir, M. E., et al., "Tissue Expression of PD-L1 Mediates Peripheral T Cell Tolerance," J. Exp. Med. 203:883-895 (2006).

Kim, T. D., et al., "Organ-Derived Dendritic Cells have Differential Effects on Alloreactive T Cells," Blood 111:2929-2940 (2008).

Kim, Y.M., et al., "Graft-Versus-Host Disease can be Separated from Graft-Versus-Lymphoma Effects by Control of Lymphocyte Trafficking with FTY720," J. Clin. Invest. 111:659-669 (2003).

Kim, Y.M., et al., "Graft-Versus-Host-Reactive Donor CD4 Cells Can Induce T Cell-Mediated Rejection of the Donor Marrow in Mixed Allogeneic Chimeras Prepared with Nonmyeloablative Conditioning," Blood 103:732-739 (2004).

Kodama, S., et al., "Islet Regeneration During the Reversal of Autoimmune Diabetes in NOD Mice," Science 302:1223-1227 (2003).

Kronenberg, M., et al., "The Unconventional Lifestyle of NKT Cells," Nat. Rev. Immunol. 2:557-568 (2002).

Kunkel, E.J., et al., "Lymphocyte CC Chemokine Receptor 9 and Epithelial Thymus-Expressed Chemokine (TECK) Expression Distinguish the Small Intestinal Immune Compartment: Epithelial Expression of Tissue-Specific Chemokines as an Organizing Principle in Regional Immunity," J. Exp. Med. 192:761-767 (2000).

Lan, F., et al., "Predominance of $NK1.1^+TCR$ Alpha $Beta^+$or $DX5^+TCR$ Alpha $Beta^+T$ Cells in Mice Conditioned with Fractionated Lymphoid Irradiation Protects Against Graft-Versus-Host Disease: "Natural Suppressor" Cells[1]," J. Immunol. 167:2087-2096 (2001).

Li, H., et al., "Mixed Allogeneic Chimerism Induced by a Sublethal Approach Prevents Autoimmune Diabetes and Reverses Insulitis in Nonobese Diabetic (NOD) Mice[1]," J. Immunol. 156:380-388 (1996).

Li, N., et al., "Anti-CD3 Preconditioning Separates GVL from GVHD Via Modulating Host Dendritic Cell and Donor T-Cell Migration in Recipients Conditioned with TBI," Blood 22:953-962 (2009).

Li, N., et al., "HDAC Inhibitor Reduces Cytokine Storm and Facilitates Induction of Chimerism that Reverses Lupus in Anti-CD3 Conditioning Regimen," PNAS 105:4796-4801 (2008).

Loetscher, P., et al., "CCR5 is Characteristic of Th1 Lymphocytes," Nature 391:344-345 (1998).

Mapara, M. Y., et al., "Expression of Chemokines in GVHD Target Organs is Influenced by Conditioning and Genetic Factors and Amplified by GVHR," Biol. Blood Marrow Transplant. 12:623-634 (2006).

Martin, P.J., "Donor CD8 Cells Prevent Allogeneic Marrow Graft Rejection in Mice: Potential Implications for Marrow Transplantation in Humans," J. Exp. Med. 178:703-712 (1993).

Martin, P.J., et al., "A Phase I-II Clinical Trial to Evaluate Removal of CD4 Cells and Partial Depletion of CD8 Cells From Donor Marrow for HLA-Mismatched Unrelated Recipients," Blood 94:2192-2199 (1999).

Marzo, A. L., et al., "Fully Functional Memory CD8 T Cells in the Absence of CD4 T Cells," J. Immunol. 173:969-975 (2004).

Merad, M., et al., "Depletion of Host Langerhans Cells Before Transplantation of Donor Alloreactive T Cells Prevents Skin Graft-Versus-Host Disease," Nat. Med. 10:510-517 (2004).

Mora, J. R., et al., "Reciprocal and Dynamic Control of CD8 T Cell Homing by Dendritic Cells from Skin- and Gut-Associated Lymphoid Tissues," J. Exp. Med. 201:303-316 (2005).

Mucida, D., et al., "Reciprocal $T_H17$ and Regulatory T Cell Differentiation Mediated by Retinoic Acid," Science 317:256-260 (2007).

Muhlbauer, M., et al., "PD-L1 is Induced in Hepatocytes by Viral Infection and by Interferon-α and -γ and Mediates T cell Apoptosis," J. Hepatol. 45:520-528 (2006).

Murai, M., et al., "Active Participation of CCR5+CD8+ T Lymphocytes in the Pathogenesis of Liver Injury in Graft-Versus-Host Disease," J. Clin. Invest. 104:49-57 (1999).

Muraille, E., et al., "Downregulation of Antigen-Presenting Cell Functions After Administration of Mitogenic Anti-CD3 Monoclonal Antibodies in Mice," Blood 94:4347-4357 (1999).

Murphy, W. J., et al., "Differential Effects of the Absence of Interferon-γ and IL-4 in Acute Graft-Versus-Host Disease After Allogenic Bone Marrow Transplantation in Mice," J. Clin. Invest. 102:1742-1748 (1998).

Nakajima, C., et al., "Induction of the Chemokine Receptor CXCR3 on TCR-Stimulated T Cells: Dependence on the Release from Persistent TCR-Triggering and Requirement for IFN-Gamma Stimulation," Eur. J. Immunol. 32:1792-1801 (2002).

Nakazawa, A., et al., "The Expression and Function of Costimulatory Molecules B7h and B7-H1 on Colonic Epithelial Cells," Gastroenterol. 126:1347-1357 (2004).

Nikolic, B., et al., "Mixed Hematopoietic Chimerism Allows Cure of Autoimmune Diabetes Through Allogeneic Tolerance and Reversal of Autoimmunity," Diabetes 53:376-383 (2004).

Nishimura, H., et al., "Autoimmune Dilated Cardiomyopathy in PD-1 Receptor-Deficient Mice," Science 291:319-322 (2001).

Nishimura, H., et al., "Development of Lupus-Like Autoimmune Diseases by Disruption of the PD-1 Gene Encoding an ITIM Motif-Carrying Immunoreceptor," Immunity 11:141-151 (1999).

Ohl, L., et al., "CCR7 Governs Skin Dendritic Cell Migration Under Inflammatory and Steady-State Conditions," Immunity 21:279-288 (2004).

Olson, T. S., et al., "Chemokines and Chemokine Receptors in Leukocyte Trafficking," Am. J. Physiol. Regul. Integr. Comp. Physiol. 283:R7-R28 (2002).

Panoskaltsis-Mortari, A., et al., "In Vivo Imaging of Graft-Versus-Host-Disease in Mice," Blood 103:3590-3598 (2004).

Patterson, B.K., et al., "Regulation of CCR5 and CXCR4 Expression by Type 1 and Type 2 Cytokines: CCR5 Expression is Downregulated by IL-10 in CD4-Positive Lymphocytes," Clin. Immunol. 91:254-262 (1999).

Pelot, M.R., et al., "Lymphohematopoietic Graft-vs.-Host Reactions Can Be Induced Without Graft-vs.-Host Disease in Murine Mixed Chimeras Established with a Cyclophosphamide-Based Nonmyeloablative Conditioning Regimen," Biol. Blood Marrow Transplant. 5:133-143 (1999).

Perruche, S., et al., "CD3-Specific Antibody-Induced Immune Tolerance Involves Transforming Growth Factor-β from Phagocytes Digesting Apoptotic T Cells," Nat. Med. 14:528-535 (2008).

Picker, L.J., et al., "A unique phenotype of Skin-Associated Lymphocytes in Humans. Preferential Expression of the HECA-452 Epitope by Benign and Malignant T Cells at Cutaneous Sites," Am. J. Pathol. 136:1053-1068 (1990).

Reddy, P., et al., "A Crucial Role for Antigen-Presenting Cells and Alloantigen Expression in Graft-Versus-Leukemia Responses," Nat. Med. 11:1244-1249 (2005).

Reiss, Y., et al., "CC Chemokine Receptor (CCR)4 and the CCR10 Ligand Cutaneous T Cell-Attracting Chemokine (CTACK) in Lymphocyte Trafficking to Inflamed Skin," J. Exp. Med. 194:1541-1547 (2001).

Ricordi, C., "Islet Transplantation: A Brave New World," Diabetes 52:1595-1603 (2003).

Rossini, A.A., "Autoimmune Diabetes and the Circle of Tolerance," Diabetes 53:267-275 (2004).

Sackstein, R., "A Revision of Billingham's Tenets: The Central Role of Lymphocyte Migration in Acute Graft-Versus-Host Disease," Biol. Blood Marrow Transplant. 12:2-8 (2006).

Schoop, R., et al., "Suppressed T-Cell Activation by IFN-γ-Induced Expression of PD-L1 on Renal Tubular Epithelial Cells," Nephrol. Dial. Transplant. 19:2713-2720 (2004).

Seung, E., et al., "Allogeneic Hematopoietic Chimerism in Mice Treated with Sublethal Myeloablation and Anti-CD154 Antibody: Absence of Graft-Versus-Host Disease, Induction of Skin Allograft Tolerance, and Prevention of Recurrent Autoimmunity in Islet-Allografted NOD/Lt Mice," Blood 95:2175-2182 (2000).

Seung, E., et al., "Hematopoietic Chimerism and Central Tolerance Created by Peripheral-Tolerance Induction Without Myeloablative Conditioning," J. Clin. Invest. 112:795-808 (2003).

Shlomchik, W. D., "Graft-Versus-Host Disease," Nat. Rev. Immunol. 7:340-352 (2007).

Shlomchik, W. D., et al., "Transplantation's Greatest Challenges: Advances in Chronic Graft-Versus-Host Disease," Biol. Blood Marrow Transplant. 13:2-10 (2007).

Sigmundsdottir, H., et al., "DCs Metabolize Sunlight-Induced Vitamin D3 to 'Program' T cell Attraction to the Epidermal Chemokine CCL27," Nat. Immunol. 8:285-293 (2007).

Slavin, S., et al., "Nonmyeloablative Stem Cell Transplantation and Cell Therapy as an Alternative to Conventional Bone Marrow Transplantation with Lethal Cytoreduction for the Treatment of Malignant and Nonmalignant Hematologic Diseases," Blood 91:756-763 (1998).

Soiffer, R.J., "T-Cell Depletion to Prevent Graft-vs-Host Disease," Hematopoietic cell transplantation. Malden: Blackwell Science Ltd. 221-233 (2004).

Stenstad, H., et al., "Differential Homing Mechanisms Regulate Regionalized Effector CD8αβ$^+$T cell Accumulation Within the Small Intestine," PNAS 104:10122-10127 (2007).

Sullivan, K.M., et al., "The Evolving Role of Blood and Marrow Transplantation for the Treatment of Autoimmune Diseases," J. Rheumatol. Suppl. 48:1-4 (1997).

Sullivan, K.M., "Graft-vs-Host Disease," Hematopoietic cell transplantation. Malden: Blackwell Science Ltd. 635-664 (2004).

Sun, J. C., et al., "CD4+ T Cells are Required for the Maintenance, not Programming, of Memory CD8+ T Cells After Acute Infection," Nat. Immunol. 5:927-933 (2004).

Sykes, M., et al., "Graft-Versus-Host-Related Immunosuppression is Induced in Mixed Chimeras by Alloresponses Against Either Host or Donor Lymphohematopoietic Cells," J. Exp. Med. 168:2391-2396 (1988).

Sykes, M., "Mixed Chimerism and Transplant Tolerance," Immunity 14:417-424 (2001).

Sykes, M., "Mechanisms of Tolerance," Hematopoietic Cell Transplantation. Malden: Blackwell Science Ltd. 300-323 (2004).

Taniguchi, M., et al., "The Regulatory Role of Valpha14 NKT Cells in Innate and Acquired Immune Response," Annu. Rev. Immunol. 21:483-513 (2003).

Terwey, T. H., et al., "CCR2 is Required for CD8-Induced Graft-Versus-Host Disease," Blood 106:3322-3330 (2005).

Tietz, W., et al., "CD4+ T Cells Migrate into Inflamed Skin Only if They Express Ligands for E- and P-Selectin," J. Immunol. 161:963-970 (1998).

Todorov, I.T., et al., "BM28, A Human Member of the MCM2-3-5 Family, is Displaced from Chromatin During DNA Replication," J. Cell. Biol. 129:1433-1445 (1995).

Turnbull, E. L., et al., "Intestinal Dendritic Cell Subsets: Differential Effects of Systemic TLR4 Stimulation on Migratory Fate and Activation In Vivo," J. Immunol. 174:1374-1384 (2005).

Varona, R., et al., "CCR6 Regulates CD4+ T-Cell-Mediated Acute Graft-Versus-Host Disease Responses," Blood 106:18-26 (2005).

Wagner, J.L., et al., "The Development of Chronic Graft-Versus-Host Disease: An Analysis of Screening Studies and the Impact of Corticosteroid Use at 100 Days After Transplantation," Bone Marrow Transplant 22:139-146 (1998).

Wakim, L. M., et al., "Dendritic Cell-Induced Memory T Cell Activation in Nonlymphoid Tissues," Science 319:198-202 (2008).

Webster, A. C., et al., "Monoclonal and Polyclonal Antibody Therapy for Treating Acute Rejection in Kidney Transplant Recipients: A Systematic Review of Randomized Trial Data," Transplantation 81:953-965 (2006).

Wekerle, T., et al., "Allogeneic Bone Marrow Transplantation with Co-Stimulatory Blockade Induces Macrochimerism and Tolerance Without Cytoreductive Host Treatment," Nat Med 6:464-469 (2000).

Welniak, L. A., et al., "Immunobiology of Allogeneic Hematopoietic Stem Cell Transplantation," Annu. Rev. Immunol. 25:139-170 (2007).

Wysocki, C. A., et al., "Differential Roles for CCR5 Expression on Donor T Cells During Graft-Versus-Host Disease Based on Pretransplant Conditioning," J. Immunol. 173:845-854 (2004).

Wysocki, C. A., et al., "Leukocyte Migration and Graft-Versus-Host Disease," Blood 105:4191-4199 (2005).

Yamazaki, T., et al., "Expression of Programmed Death 1 Ligands by Murine T Cells and APC," J. Immunol. 169:5538-5545 (2002).

Yang, Y.G., et al., "Donor-Derived Interferon γ is Required for Inhibition of Acute Graft-Versus-Host Disease by Interleukin 12," J. Clin. Invest. 102:2126-2135 (1998).

Yang, F., et al., "Spontaneous Development of Liver Tumors in the Absence of the Bile Acid Receptor Farnesoid X Receptor," Cancer Res. 67:863-867 (2007).

Yi, T., et al., "Absence of Donor Th17 Leads to Augmented Th1 Differentiation and Exacerbated Acute Graft-Versus-Host Disease," Blood 112:2101-2110 (2008).

Yoshida, A., et al., 2004. CD8 T Cell of Donor Splenocyte Mixed with Bon Marrow Cells is More Effective Than CD4 T Cell for Induction of Donor-Specific Tolerance in Sublethally Irradiated Mice. Transplantation Proceedings 36:2418-2422.

Youngnak-Piboonratanakit, P., et al., "The Expression of B7-H1 on Keratinocytes in Chronic Inflammatory Mucocutaneous Disease and its Regulatory Role," Immunol. Lett. 94:215-222 (2004).

Yu, X.Z., et al., "CD28 Ligation Induces Transplantation Tolerance by IFN-γ-Dependent Depletion of T Cells that Recognize Alloantigens," J. Clin. Invest. 113:1624-1630 (2004).

Zeng, D., et al., "Bone Marrow NK1.1$^-$ and NK1.1$^+$T Cells Reciprocally Regulate Acute Graft Versus Host Disease," J. Exp. Med. 189:1073-1081 (1999).

Zeng, D., et al., "Different Patterns of Migration and Expansion of Blood and Marrow CD4 T Cells in Lymphoid and Non-Lymphoid Tissues Result in a Different Capacity to Induce Graft-vs-Host Disease," The American Association of Immunologists 90th Anniversary Annual Meeting. Denver, Colorado: FASEB C59 (2003).

Zeng, D., et al., "Suppression of Graft-Versus-Host Disease by Naturally Occurring Regulatory T Cells," Transplantation 77:S9-S11 (2004).

Zeng, D., et al., "Unique Patterns of Surface Receptors, Cytokine Secretion, and Immune Functions Distinguish T Cells in the Bone Marrow from Those in the Periphery: Impact on Allogenic Bone Marrow Transplantation," Blood 99:1449-1457 (2002).

Zhang, Y., et al., "APCs in the Liver and Spleen Recruit Activated Allogenic CD8+ T Cells to Elicit Hepatic Graft-Versus-Host Disease," J. Immunol. 169:7111-7118 (2002).

Zhang, C., et al., "Donor CD4+ T and B Cells in Transplants Induce Chronic Graft-Versus-Host Disease with Autoimmune Manifestations," Blood 107:2993-3001 (2006).

Zhao, D., et al., "In Vivo Activated CD103+CD4+ Regulatory T Cells Ameliorate Ongoing Chronic Graft-Versus-Host Disease," Blood 112:2129-2138 (2008).

* cited by examiner

METHODS FOR CONDITIONING A SUBJECT FOR HEMATOPOIETIC CELL TRANSPLANTATION

PRIORITY CLAIM

This application claims the benefit of U.S. Provisional Patent Application Ser. No. 61/016,436, filed Dec. 21, 2007, the disclosure of which is incorporated herein by reference in its entirety, including drawings.

BACKGROUND

Allogeneic hematopoietic cell transplantation (HCT) is a curative therapy for hematological malignancies as well as refractory autoimmune diseases such as systemic lupus erythematosus (SLE) (Shizuru 2004; Sullivan 2004; Sykes 2005). HCT results in allogeneic hematopoietic chimerism. For subjects with hematological malignancies, HCT allows for administration of higher and more potentially effective dosages of chemotherapy and radiotherapy. For subjects with abnormal nonmalignant lymphohematopoietic systems, HCT allows for replacement of the abnormal lymphohematopoietic system with a healthy one. HCT is often referred to as bone marrow transplantation (BMT). However, hematopoietic stem cells for use in HCT can be collected from bone marrow, peripheral blood, or umbilical cord blood.

In classical HCT, recipients are conditioned with total body irradiation (TBI) and/or high dose chemotherapy. However, both TBI and chemotherapy are highly toxic, even at reduced intensity. In addition, TBI and chemotherapy play a critical role in initiating graft versus host disease (GVHD) (Ferrara 2004). Toxicity and GVHD have limited the application of HCT. Therefore, there is a need for improved methods of conditioning a recipient for HCT.

SUMMARY

In certain embodiments, compositions are provided comprising one or more anti-CD3 compounds and one or more histone deacetylase inhibitors. In certain embodiments, the one or more anti-CD3 compounds comprise one or more anti-CD3 antibodies and the one or more histone deacetylase inhibitors comprise suberoylanilide hydroxamic acid.

In certain embodiments, methods are provided for conditioning a recipient for hematopoietic cell transplantation by administering a therapeutically effective amount of one or more anti-CD3 compounds and a therapeutically effective amount of one or more histone deacetylase inhibitors. In certain embodiments, the one or more anti-CD3 compounds comprise one or more anti-CD3 antibodies and the one or more histone deacetylase inhibitors comprise suberoylanilide hydroxamic acid.

In certain embodiments, methods are provided for generating chimerism in a recipient by administering a therapeutically effective amount of one or more anti-CD3 compounds and a therapeutically effective amount of one or more histone deacetylase inhibitors. In certain embodiments, the one or more anti-CD3 compounds comprise one or more anti-CD3 antibodies and the one or more histone deacetylase inhibitors comprise suberoylanilide hydroxamic acid.

In certain embodiments, methods are provided for preconditioning a recipient before conditioning the recipient for hematopoietic cell transplantation by administering a therapeutically effective amount of one or more anti-CD3 compounds. In other embodiments, compositions comprising one or more anti-CD3 compounds are provided for preconditioning a recipient for hematopoietic cell transplantation.

DETAILED DESCRIPTION

Figure 1:
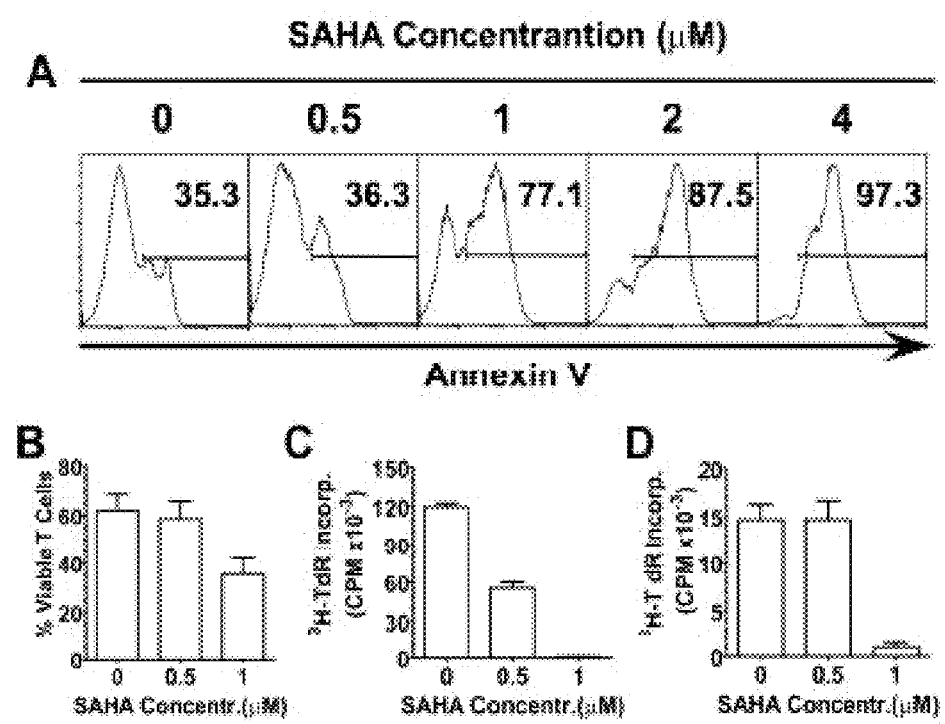
FIG. 1: A. BALB/c spleen cells ($0.5 \times 10^6$) were stimulated with plate-bound anti-CD3 in culture medium with titrated concentrations of SAHA (0~4 µM) for 72 hours. Thereafter, cells were stained with anti-TCRαβ, DAPI, and Annexin V. TCRαβ+ cells were gated and shown in a histogram of Annexin V. The percentages of Annexin $V^+$ cells are shown for each culture. One representative FACS pattern of four replicated experiments is shown. The Mean±SE of the percentage of Annexin V+ cells under different SAHA concentration (0~4 µM) were 38.1±6.5%, 41.5±7.2%, 64.4±6.6%, 85.5±2.7%, and 97.1±1.5%. B. Percentage of viable T cells among total T cells in the culture with SAHA at concentration of 0~1 µM. C. T cell proliferation by anti-CD3-stimulation with SAHA at concentration of 0~1 µM. D. T cell proliferation by allo-APC stimulation with SAHA at concentration of 0~1 µM. B-D show Mean±SE of four replicated experiments.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

The following abbreviations are used herein: APC, antigen-presenting cell; BLI, bioluminescent imaging; BM, bone marrow; BMT, bone marrow transplantation; CFSE, CarboxyFluoroscein Succinimidyl Ester; DC, dendritic cell; FACS, fluorescence-activated cell sorting; FITC, fluorescein; GVHD, graft-versus-host disease; GVL, graft-versus-leukemia; HAT, histone acetyltransferase; HCT, hematopoietic cell transplantation; HDAC, histone deacetylase; LPS, lipopolysaccharide; mAb, monoclonal antibody; MLR, mixed lymphocyte reaction; NKT, natural killer T; NOD, non-obese diabetic; SAHA, suberoylanilide hydroxamic acid; SLE, systemic lupus erythematosus; TBI, total body irradiation; TCD, T-cell depleted.

The term "recipient" or "host" as used herein refers to a subject receiving transplanted or grafted tissue. These terms may refer to, for example, a subject receiving an administration of donor bone marrow, donor peripheral blood, donor umbilical cord blood, donor T cells, or a pancreatic islet graft. The transplanted tissue may be derived from a syngeneic or allogeneic donor.

The term "donor" as used herein refers to a subject from whom tissue is obtained to be transplanted or grafted into a recipient or host. For example, a donor may be a subject from whom bone marrow, peripheral blood, umbilical cord blood, T cells, or other tissue to be administered to a recipient or host is derived.

The term "chimerism" as used herein refers to a state in which one or more cells from a donor are present and functioning in a recipient or host. Recipient tissue exhibiting "chimerism" may contain donor cells only (complete chimerism), or it may contain both donor and host cells (mixed chimerism). "Chimerism" as used herein may refer to either transient or stable chimerism.

The phrase "therapeutically effective amount" as used herein refers to an amount of a compound that produces a desired therapeutic effect. The precise therapeutically effective amount is an amount of the composition that will yield the most effective results in terms of efficacy in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy (Gennaro ed. 20$^{th}$ edition, Williams & Wilkins PA, USA) (2000).

The term "simultaneously" as used herein with regards to administration of two or more compounds means that the compounds are administered at the same or nearly the same time. For example, two or more compounds are considered to be administered "simultaneously" if they are administered via a single combined administration, two or more administrations occurring at the same time, or two or more administrations occurring in succession.

Recent studies have shown that TBI and high-dose chemotherapy play a critical role in the induction of GVHD following HCT, and that higher doses of irradiation are associated with more severe GVHD (Ferrara 2004). The conditioning procedures cause tissue damage, release of proinflammatory cytokines and chemokines, and activation of host antigen presenting cells (APCs), which results in a proinflammatory cascade and donor alloreactive T cell infiltration of GVHD target tissues (Shlomchik 1999; Teshima 2002; Chakraverty 2006). Therefore, radiation-free and GVHD preventive conditioning regimens for allogeneic HCT are highly desirable. Disclosed herein are various compositions and methods for establishing chimerism via HCT without inducing GVHD.

It has been reported that transplantation of a large dose of donor bone marrow (BM) cells and administration of a co-stimulatory blockade (i.e., anti-CD40L antibodies) induces mixed chimerism in non-autoimmune mice (Wekerle 2000), but this regimen has not been shown to work in autoimmune mice. We have previously reported that infusion of donor CD8+ T or CD4+ T-depleted spleen cells and BM cells induced chimerism without GVHD in both non-autoimmune and autoimmune non-obese diabetic (NOD) mice (Liang 2005; Zhang 2007a; Zhang 2007b).

The mechanisms of GVHD prevention in the anti-CD3-conditioned recipients include confining donor CD8+ T cells to host lymphohematological tissues and tolerizing the alloreactive T cells (Zhang 2007). The anti-CD3-conditioning regimen allows donor CD8+ T cells to mediate graft versus host leukemia (GVL) activity and graft versus autoimmune (GVA) activity without causing GVHD (Liang 2005; Zhang 2007a; Zhang 2007b). In addition, the chimeric NOD recipients with chimerism established by anti-CD3 conditioning showed regeneration of islet β cells and reversal of diabetes (Zhang 2007b). Therefore, the anti-CD3-conditioning regimen has the potential to promote allogeneic HCT for treating autoimmune diseases. However, anti-CD3-conditioning often causes a cytokine storm syndrome, which includes hypothermia and hypoglycemia. The cytokine storm syndrome and the high-dose donor BM cells required for the induction of chimerism hamper the clinical application of a purely anti-CD3-based conditioning regimen.

Chromatin remodeling by acetylation or deacetylation of histones plays a critical role in the regulation of gene expression (Marks 2001; Roth 2001). Histone acetylation is controlled by two classes of enzymes: histone acetyltransferases (HATs) add acetyl groups to lysine residues, while histone deacetylases (HDACs) remove the acetyl groups (Marks 2001). Acetylation of histones relaxes chromatin structure, allowing the binding of transcription factors and promoting transcription. In contrast, deacetylation of histones condenses chromatin structure and represses gene transcription (Marks 2001; Roth 2001). Inhibiting the deacetylation of histones results in hyperacetylation and modifies gene expression either positively or negatively in a cell type-specific manner (Marks 2001).

Suberoylanilide hydroxamic acid (SAHA), also known as Vorinostat, contains a hydroxamic acid moiety that binds to the zinc-containing pocket in the catalytic site of HDAC 6 and causes reversible inhibition of the enzyme (Marks 2003). It has been reported that SAHA selectively increases the expression of many genes in tumor cells, causing them to undergo cell cycle arrest and apoptosis (Xu 2007). Although micromolar concentrations of SAHA are required for anti-tumor effects, nanomolar concentrations of SAHA can reduce the secretion of inflammatory cytokines such as TNF-α, IFN-γ, IL-1β, and IL-12 by non-malignant cells (Leoni 2002). It has been reported that administration of low-dose SAHA reduced serum levels of inflammatory cytokines and ameliorates GVHD without inhibiting donor T cell function and graft-versus-leukemia (GVL) activity (Reddy 2004; Leng 2006).

Disclosed herein are experiments showing that administration of high concentrations of SAHA (i.e., 1 μM or greater) in conjunction with anti-CD3 conditioning augments apoptosis, and that administration of low concentrations of SAHA (less than 1 μM) in conjunction with anti-CD3 conditioning inhibits the proliferative and cytotoxic activity of the anti-CD3-activated residual host T cells. Administration of low-dose SAHA during anti-CD3 conditioning ameliorates cytokine storm syndrome and ameliorates conditions associated with cytokine storm such as hypothermia. In addition, conditioning with anti-CD3 and SAHA augments induction of chimerism and allows induction of complete chimerism without causing GVHD. This is consistent with the observed ability of high concentration SAHA to augment apoptosis and the ability of low concentration SAHA to reduce the proliferative and cytotoxic activity of T cells activated by anti-CD3. The residual T cells in the recipients conditioned with anti-CD3 and low-dose SAHA have a reduced capacity to reject donor cells.

The results disclosed herein constitute the first demonstration that an anti-tumor chemoreagent can be used for conditioning of allogeneic recipients without induction of GVHD. The radiation-free and GVHD-preventative conditioning regimen disclosed herein may promote the application of allogeneic HCT for treating refractory autoimmune disease, in addition to the treatment of hematological malignancies. Therefore, provided herein are various compositions and methods for conditioning a recipient for HCT using a combination of one or more anti-CD3 compounds, such as for example antibodies, and one or more HDAC inhibitors. In addition, methods are provided for inducing partial or complete chimerism in a subject comprising conditioning the subject with one or more anti-CD3 compounds, such as for example antibodies, and one or more HDAC inhibitors. Further provided herein are methods of treating lupus in a subject comprising conditioning the subject with one or more anti-CD3 compounds, such as for example antibodies, and one or more HDAC inhibitors, then performing HCT. The anti-CD3/SAHA conditioning regimen disclosed herein cured systemic lupus in NZB/W F1 mice with severe glomerulonephritis.

In allogeneic HCT, both GVHD and GVL activity are predominantly mediated by donor T cells in bone marrow graft (Reddy 2005, Chakraverty 2007, Shlomchik 2007, Welniak 2007). Donor T cells are activated in host lymphoid tissues and then migrate to epithelial GVHD target tissues (i.e. gut, liver, lung, and skin) to mediate GVHD (Ferrara 2004, Panoskaltsis-Mortari 2004, Beilhack 2005). Studies have shown that inhibition of donor T cell migration to GVHD target tissues prevents GVHD but retains GVL activities in lympho-hematological tissues (Kim 2003, Zhang 2007). In addition, host DCs in tissues may attract activated donor T cells to GVHD target tissues, because depletion of APCs in liver were shown to markedly reduced activated donor T migration into liver (Zhang 2002). It has been proposed that tissue inflammatory chemokines attract donor T cell migration to GVHD target tissues after TBI-conditioning (Chakraverty 2006), and the chemokines are secreted by tissue macrophage and tissue DCs as well as infiltrated donor T cells (Mapara 2006). However, it is not yet clear which cells are the initial ones in chemokine release. It has been reported that, in the case of viral infection, plasmacytoid DCs initiate the complex chemokine and cytokine network (Decalf 2007). Therefore, plasmacytoid DCs in GVHD target tissues may also play an initial role in chemokine release after TBI-conditioning. Modulation of DC's tissue distribution has been suggested to regulate immune responses. Disclosed herein are various compositions and methods for modulating host DC subset tissue distribution and inhibiting donor T cell migration to GVHD target tissues.

Disclosed herein are experiments showing that anti-CD3 preconditioning results in separation of GVL from GVHD in recipients later conditioned for HCT. GVHD prevention resulted from reduction of donor T cell migration to GVHD target tissues, which was associated with inhibition of donor T cell expression of homing and chemokine receptors as well as inhibition of GVHD target tissue expression of chemokines. These results constitute the first demonstration that modulation of DC subset tissue distribution before HCT (i.e. prevention of tissue DC migration to draining LN) leads to confinement of donor T cells to lympho-hematological tissues and separation of GVL from GVHD. The preconditioning regimen disclosed herein may promote the application of allogeneic HCT for treating refractory autoimmune disease, in addition to the treatment of hematological malignancies. Therefore, provided herein are compositions and methods for preconditioning a recipient before conditioning the recipient for HCT using a combination of one or more anti-CD3 compounds, such as for example antibodies. Also provided are compositions and methods for reducing GVHD in a subject receiving TBI prior to HCT comprising preconditioning the subject prior to TBI with one or more anti-CD3 compounds.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Example 1

Materials and Methods

Mice:
C57BL/6 ($H-2^b$, CD45.2), congenic C57BL/6 ($H-2^b$, CD45.1), BALB/c ($H-2^d$), female NZB/W F1 ($H-2^{d/z}$) mice were purchased from The Jackson Laboratory (Bar Harbor, Me.) and NCI Laboratories (Frederick, Md.). All animals were maintained in a pathogen-free room at City of Hope Animal Research Facilities (Duarte, Calif.). Animal use protocols were approved by the institutional review committee.

Flow Cytometric Analysis (FACS) and Cell Sorting:

The following anti-mouse mAbs were purchased from BD Biosciences Pharmingen (San Diego, Calif.), eBioscience (San Diego, Calif.), and R&D Systems (Minneapolis, Minn.): TCRβ (H57-597), CD4 (RM4-5), CD8α (53-6.7), B220 (RA3-6B2), CD11b/Mac-1 (M1/70), Gr-1 (RB6-8C5), CD45.1 (A20), H-$2^b$ (AF6-88.5), H-$2^d$ (34-2-12), CD11c (HL3), α4β7 (DATK32), CD103 (M290), CCR9 (CW-1.2), CCR4 (1G1), CCR10 (248918), CCR5 (HM-CCR5), CXCR3 (1C6/CXCR3), PDCA-1 (JF05-1C2.4.1), E-selectin/Fc Chimera, P-selectin/Fc chimera, and anti-IFN-γ (2E2). FACS was performed with a four-laser MoFlo Immunocytometry System (Dako Cytomation, Fort Collins, Colo.) and data were analyzed with FlowJo software (Tree Star, San Carlos, Calif.), as previously described (Liang 2005; Zhang 2007a; Zhang 2007b). The apoptosis measuring kit (anti-annexin V Ab) was purchased from BD Pharmingen. The FoxP3 staining kit was purchased from eBioscience CD4-SPL cells from donor spleen were negatively selected with anti-CD4-FITC and anti-FITC micromagnetic beads purchased from Miltenyi Biotec (Auburn, Calif.), as previously described (Liang 2005; Zhang 2007a; Zhang 2007b).

CD11$^+$ DCs in lamina propria, liver, LN, and spleen were collected as previously described (Johansson-Lindbom 2005, Drakes 2004). CD103$^+$ and CD103$^-$ CD11$^+$ DC subsets (purity >99%) were isolated with flow cytometry sorting after magnetic enrichment of CD11c$^+$ DCs. MNC cells from liver and gut were processed and collected as previously described (Zeng 2002). MNCs from skin were collected as following: back skin (3×3 cm$^2$) were cut into small pieces and digested in RPMI containing 10 mM HEES (Irvine Scientific), 0.01% DNase (Sigma), 0.27% collagenase (Sigma), and 1000 U of hyaluronidase at 37° C. for 1 hour. Skin MNCs were then isolated by Lymphocyte M.

Chemoreagents:

SAHA (Vorinostat) was provided by Merck Pharmaceutical. SAHA was dissolved in DMSO at 1 M and aliquots were kept at −20° C. For in vitro assays, SAHA was diluted with culture media. For in vivo assays, SAHA was diluted in 45% PEG400 (Sigma) and 55% water.

Conditioning of Recipients and HCT:

Production of anti-CD3 mAb (145-2C11) was performed as described previously (Zhang 2007a). Recipient mice were i.v. injected with anti-CD3 (5 µg/g) on day-9 and i.p. injected with SAHA (40~200 µg/g) twelve and one hours prior to anti-CD3 injection, then SAHA was injected daily for seven days after anti-CD3 injection. On day 0, the conditioned recipients were transplanted with donor BM cells (2×10$^6$/g, about 50×10$^6$/mouse) and CD4+ T-depleted spleen cells (4×10$^6$/g). The BM and spleen cells were injected again seven days after the first injection. The recipients were monitored for clinical signs of GVHD and checked for chimerism as previously described (Liang 2005; Zhang 2007a; Zhang 2007b). Proteinuria in NZB/W F1 mice was measured on a scale of 1-4+ using a colorimetric assay for albumin (Albustix, Ind.). Mice were considered to have proteinuria if three consecutive urine samples were greater than 2+, according to the scale (100 mg/dL), as described previously (Zeng 2000; Zeng 2003).

CarboxyFluoroscein Succinimidyl Ester (CFSE)-Labeling of Spleen Cells:

Splenocytes were suspended at 1-3×10$^7$ cells/ml, and CFSE (Invitrogen Corp.) was added at a final concentration of 2.5 µM. Cells were incubated at 37° C. for ten minutes, as previously described (Morris 2005).

In Vivo Cytotoxicity Assay and Mixed Lymphocyte Reaction (MLR):

At day 5 after HCT, recipients were injected with 20×10$^6$ unlabeled splenocytes from congenic donor-type C57BL/6 (H-$2^b$, CD45.1) and 20×10$^6$ CFSE-labeled splenocytes from host-type BALB/c (H-$2^d$). Eighteen hours later, splenocytes were harvested and stained with PE-conjugated anti-CD45.1. The percentages of remaining CD45.1$^+$ and CFSE-labeled cells were determined by FACS analysis. The in vivo cytotoxic activity of residual host T cells was reflected by the ratio of residual CD45.1$^+$ donor-type cells versus residual CFSE-labeled host-type cells. This assay system was also previously described (Morris 2005). The MLR assay was performed as previously described (Zhang 2007a).

Histopathology of Kidney:

Kidney tissues were fixed in formalin before embedding in paraffin blocks. Tissue sections were stained with hematoxylin and eosin as described previously (Liang 2005; Zhang 2007a; Zhang 2007b). The immunofluorescent staining was performed with frozen tissue slides. Staining and image preparation procedures were previously described (Liang 2005; Zhang 2007a; Zhang 2007b).

Measurement of Cytokines and Antibodies in Serum and Culture Supernatants:

Serum cytokines (IL-2, IFN-γ, TNF-α, and IL-6) were measured using ELISA kits (BD Biosciences Pharmingen) as previously described (Zhang 2007a). Anti-dsDNA IgG was measured with ELISA as previously described (Zeng 2000; Zeng 2003). Anti-dsDNA titers are expressed in units/ml, using a reference-positive standard of pooled serum from 6- to 7-month-old NZB/W F1 mice. A 1:100 dilution of this standard serum was arbitrarily assigned a value of 100 U/ml.

Preconditioning of Recipients Followed by Conditioning of Recipients and HCT:

Production of anti-CD3 mAb (145-2C11) was performed as described previously (Zhang 2007a). Recipient BALB/c mice were injected i.v. with anti-CD3 (5 µg/g) on day-9 and were given sublethal total body irradiation (TBI, 800 rads) on day 0, then, the recipients were transplanted with donor TCD-BM cells (5×10$^6$) and whole spleen cells (2.5~5×10$^6$). For GVL experiments, Luc$^+$ BCL1 cells (0.5×10$^6$) were injected i.p. at the same time donor BM and spleen cells were injected i.v. In vivo imaging of tumor growth was performed as previously described (Zhang 2007a). The recipients were monitored daily for survival and every 5 days for body weight changes and clinical signs of GVHD. The clinical scoring system was previously described (Chakraverty 2006, Yi 2008).

GVHD Histopathology and Scoring

Colon, liver, and skin specimens were fixed in formalin before embedding in paraffin blocks. Tissue sections were stained with H&E as described previously (Zhang 2007a). Assessment of tissue damage was performed based on scoring system previously described (Yi, 2008; Cooke, 1996, and Kaplan, 2004).

Quantification of Chemokine Expression by Real-Time RT-PCR

Isolation of total tissue RNA and synthesis of first strand cDNA were described previously (Yang 2007, Yi 2008). mRNA was quantified by real-time quantitative PCR using Applied Biosystems 7300 Fast Real-Time PCR System (Applied Biosystems, Forest City, Calif.). The primers for chemokines were previously described in following publications: Ccl3-5 (Murai 1999), Ccl17 (Beaty 2007), Ccl22 (Beaty 2007), Ccl25 (Stenstad 2007), Ccl27 (Hieshima 2004), Ccl28 (Hieshima 2004), and Cxcl9-11 (Yi 2008). Relative expression levels of genes were normalized within each sample to the house keeping gene GAPDH and were presented relative to the expression in syngeneic transplantation recipients, in which irradiated BALB/c recipients were injected with $5 \times 10^6$ syngeneic TCD-BM cells as previous described (Yi 2008).

MLR and In Vitro Inducing Donor T Cell Expression of Homing and Chemokine Receptors Sorted $CD4^+$, $CD8^+$, or $CD4^+/CD8^+$ T cells ($2 \times 10^5$) from spleen of donor C57BL/6 mice were cultured with $CD11c^+$ DCs ($10^5$) from BABL/c host in a U-bottom 96-well plate for 4 days. The T cell homing and chemokine receptor expression was measured by flow cytometry and the T cell proliferation was measured by $^3$H-TdR incorporation, which were previously described (Zhang 2007a).

Statistical Analysis:

Comparison of survival groups was analyzed using the log-rank test with Prism version 4.0 (GraphPad, San Diego, Calif.). Comparison of two means was analyzed using the unpaired two-tailed Student t-test.

Example 2

Effect of SAHA Administration on Apoptosis and Proliferation of Anti-CD3-Activated T Cells SAHA has been shown previously to mediate apoptosis of growing tumor cells (Xu 2007) and inhibit proliferation of autoreactive T cells (Mishra 2003). The effect of SAHA on T cells that were activated by anti-CD3 mAb was examined. BALB/c spleen cells were stimulated with plate-bound anti-CD3 in culture medium with SAHA at various concentrations from 0.5 to 4 µM or solvent DMSO for 72 hours. SAHA augmented T cell apoptosis in a dose-dependent manner. While 0.5 µM SAHA showed little augmentation of T cell apoptosis compared to cells stimulated with anti-CD3 alone, 1 µM SAHA augmented apoptosis by about 2-fold, 2 µM SAHA augmented apoptosis by about 3-fold, and 4 µM SAHA resulted in apoptosis of nearly all T cells ($P<0.01$, FIG. 1A). Cells cultured with medium alone and cells cultured with SAHA alone showed little apoptosis (data not shown). Interestingly, although 0.5 µM SAHA did not significantly change apoptosis or survival rates of the anti-CD3-activated T cells (FIGS. 1A and B), it inhibited the proliferation of the T cells by 2-fold ($P<0.01$, FIG. 1C). Although 40% of the residual T cells in the 1 µM SAHA culture were annexin $V^-$ live cells, they showed no proliferation at all ($P<0.01$, FIG. 1C). Consistent with previous reports (Reddy 2004; Leng 2006), 0.5 µM SAHA did not inhibit donor T cells stimulated with allo-APCs, but 1 µM SAHA markedly inhibited T cell proliferation (FIG. 1D). These results indicate that high concentrations (>1 µM) of SAHA augment apoptosis and low-concentrations (<1 µM) of SAHA inhibit the proliferation of the anti-CD3 activated T cells.

Example 3

Effect of SAHA Administration on Cytokine Storm Triggered by Anti-CD3 Conditioning One of the side effects of anti-CD3-conditioning is the cytokine storm triggered by anti-CD3 activation of T cells. Elevated levels of TNF-α during the cytokine storm cause hypothermia, which results in an inactive appearance in mice (Alegre 1990). To determine the effect of SAHA administration on the cytokine production triggered by anti-CD3 conditioning, BALB/c spleen cells ($0.5 \times 10^6$) were stimulated with plate-bound anti-CD3 in culture medium with 0.5 or 1 µM SAHA. Supernatants were harvested at 24, 48, and 72 hours after culture, and IL-2, IFN-γ, TNF-α, and IL-6 concentrations were measured by ELISA. After anti-CD3-stimulation, IL-2 concentration peaked at 48 hours, and IFN-γ, TNF-α, and IL-6 all peaked at 72 hours after culture. Addition of 0.5 µM SAHA to the culture reduced cytokine production significantly at all time points ($P<0.05$, FIG. 2A), and addition of 1 µM SAHA to the culture made all four cytokines nearly undetectable ($P<0.01$, FIG. 2A).

Figure 2:
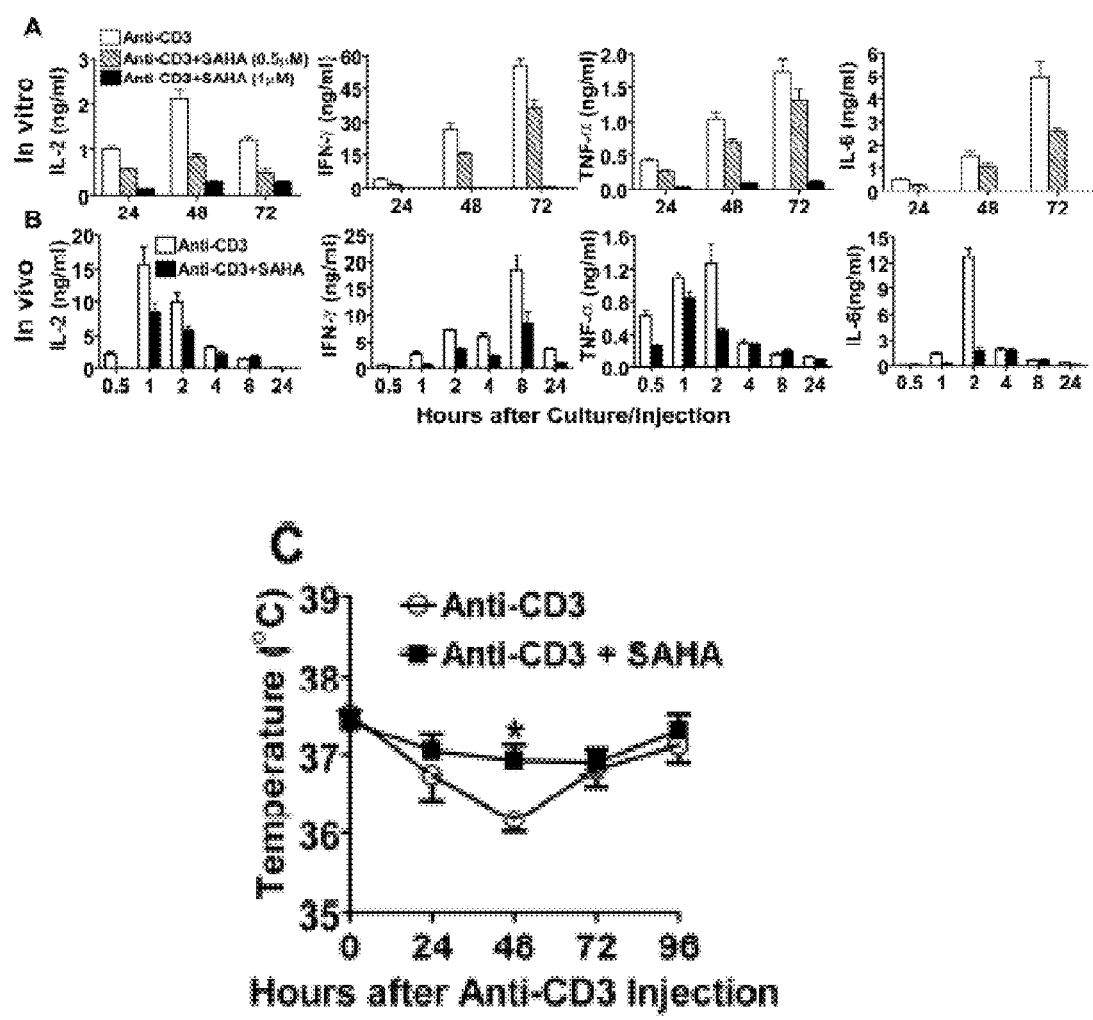
FIG. 2: A. BALB/c spleen cells ($0.5 \times 10^6$) were stimulated with plate-bound anti-CD3 in the presence of SAHA at concentrations of 0, 0.5, and 1 µM. IL-2, IFN-γ, TNF-α, and IL-6 in culture supernatant were measured at 24, 48, and 72 hours after culture. Mean±SE of four replicated experiments are shown. B. BALB/c mice were injected i.v. with anti-CD3 (5 µg/g) with or without co-injection of SAHA (40 µg/g) twelve and one hours prior to anti-CD3 injection. Serum cytokines were measured kinetically (0.5~24 hours) after anti-CD3 injection. Mean±SE of four mice at each time point is shown. C. Kinetic body temperature change of mice injected with anti-CD3 alone or anti-CD3 and SAHA. There were seven mice in each group.

Next, BALB/c mice (>16 weeks of age) were injected with anti-CD3 (5 µg/g) alone or anti-CD3 and SAHA at 40, 100, or 200 µg/g. Sera were harvested kinetically at 0.5, 1, 2, 4, 8, and 24 hours after injection for the measurement of cytokines. The mice were also measured for body temperature at the same time. After injection of anti-CD3 alone, serum IL-2 levels peaked at 1 hour, serum IFN-γ levels peaked at 8 hours, serum TNF-α, and IL-6 levels peaked at 2 hours (FIG. 2B). All serum cytokine levels fell back to background levels at 24 hours after injection (FIG. 2B). Interestingly, the mice started to look sick 24 hours after injection and appeared to be least active at 48 hours, then recovered and looked fairly normal again at 96 hours. The body temperature of the mice reached its lowest level 48 hours after injection, and then recovered to nearly normal levels at 96 hours (FIG. 2C).

Co-injection of SAHA at a dose of 40 µg/g reduced serum levels of IL-2, IFN-γ, TNF-α, and IL-6 by more than 2-fold at the peak time points as compared to mice injected with anti-CD3 alone ($P<0.01$, FIG. 2B). Co-injection of SAHA also significantly reduced hypothermia ($P<0.01$, FIG. 2C), and the treated mice appeared much more active. Co-injection of SAHA at a dose of 100 µg/g resulted in similar serum cytokine reduction and improvement in hypothermia as compared to the mice co-injected with SAHA at 40 µg/g (data not shown). However, co-injection of SAHA at a dose of 200 µg/g caused the mice to develop severe diarrhea and 30% of the mice died five days after anti-CD3-conditioning, although they exhibited reductions in serum cytokine levels that were similar to those of mice co-injected with SAHA at 40 µg/g (data not shown). Taken together, these results indicate that administration of a low dose ($\leq 100$ µg/g) of SAHA ameliorates cytokine storm syndrome triggered by mitogenic anti-CD3. Reduction of IL-2 production by SAHA may contribute to reduction of T cell proliferation, since IL-2 plays a critical role in T cell proliferation.

Example 4

Induction of Chimerism Following Conditioning with Both SAHA and Anti-CD3

Figure 3:
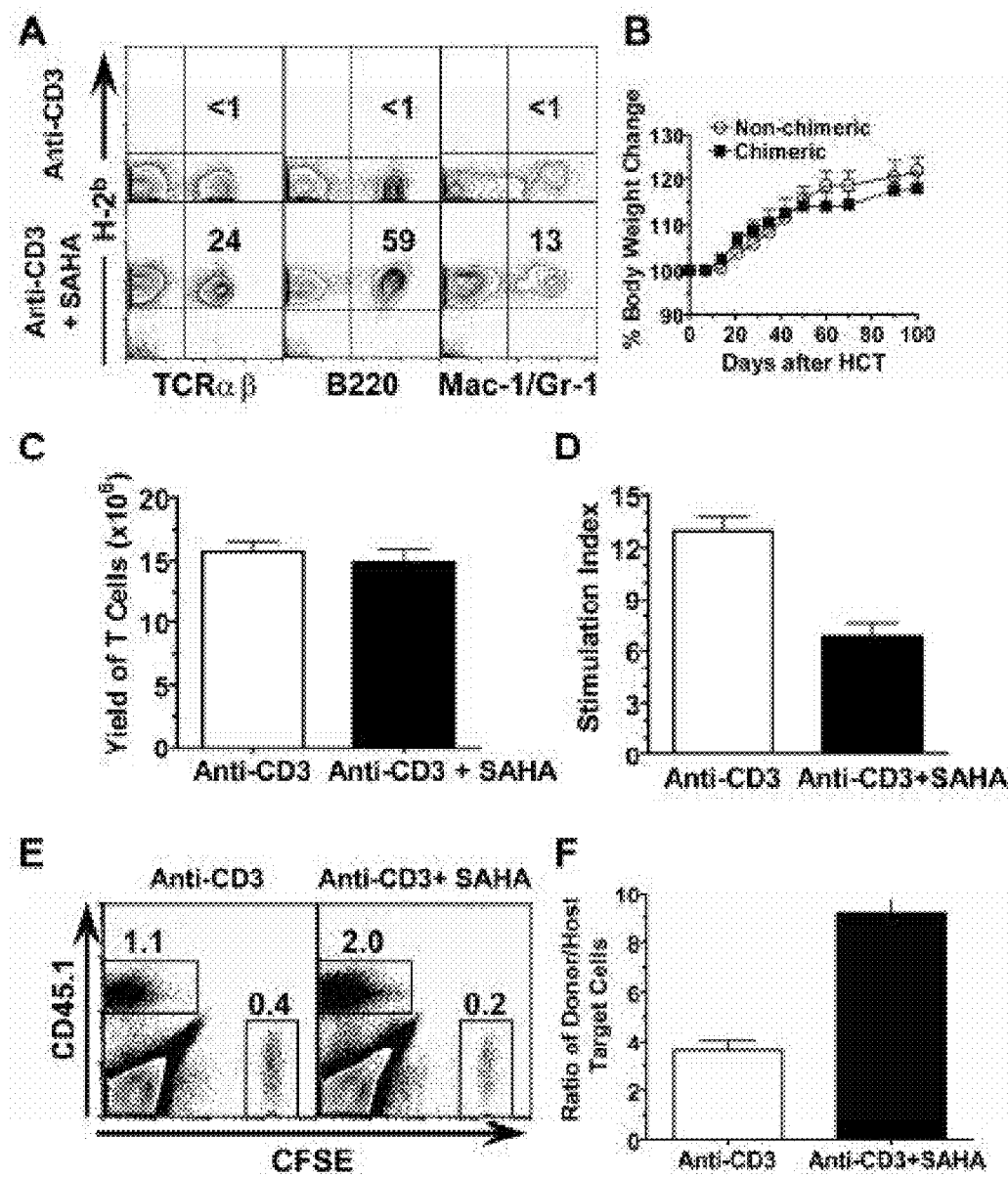
FIG. 3. Old (>16 weeks) BALB/c mice were conditioned with anti-CD3 alone or anti-CD3 and SAHA and transplanted with C57BL/6 donor BM ($2 \times 10^6$) and CD4+ T-depleted spleen cells ($4 \times 10^6$). The recipients were monitored for clinical signs of GVHD daily and body weight weekly. A. Eight weeks after HCT, blood mononuclear cells were stained for H-2b (donor marker), TCRαβ, B220, and Mac-1/Gr-1. The percentages of donor T, B, and macrophage cells are shown. One representative of twelve mice in each group is shown. B. Body weight change curves of HCT recipients conditioned with anti-CD3 alone (nonchimeric) or anti-CD3 plus SAHA (chimeric). There were 12 mice in each group. Mean±SE is shown at each time point. C. Yield of residual DAPI-live T cells in spleen of mice conditioned with anti-CD3 or anti-CD3 plus SAHA 9 days after anti-CD3 injection at the day of HCT. D. Sorted T cells ($0.2 \times 10^6$) from the spleen of conditioned BALB/c mice nine days after anti-CD3 injection were stimulated with C57BL/6 DCs ($0.1 \times 10^6$) for five days. The proliferation was measured with 3H-TdR incorporation, and the stimulation index was calculated by formula: {[CPM of responder×stimulator]−[CPM of responder alone]}÷[CPM of responder alone]. Mean±SE of four mice in each group is shown. E. Five days after HCT, donor-type spleen cells from congenic C57BL/6 (CD45.1) and CFSE-labeled host type spleen cells from BALB/c were injected into recipients conditioned with anti-CD3 alone or anti-CD3 plus SAHA. Eighteen hours later, spleen cells were harvested and stained with anti-CD45.1. Staining is shown in CD45.1 versus CFSE. One representative FACS pattern of four mice in each group is shown. The Mean±SE of $CD45.1^+$ or $CFSE^+$ cells in recipients conditioned with anti-CD3 alone versus recipients conditioned with anti-CD3 plus SAHA were 1.21±0.07% versus 1.80±0.08% or 0.35±0.03% versus 0.20±0.01%. F. The ratio of residual CD45.1+ donor-type cells versus CFSE+ host-type cells were calculated, and Mean±SE of four recipients in each group is shown.

Conditioning with anti-CD3 alone was insufficient for induction of chimerism in old (>12 weeks) recipients, although it was sufficient in young (<8 weeks old) recipients (Zhang 2007). Therefore, the ability of low-dose SAHA to augment induction of chimerism in old recipients was tested. Accordingly, old (>16 weeks) BALB/c mice were conditioned with anti-CD3 alone or with a combination of anti-CD3 and SAHA (40 µg/g). Nine days after conditioning, mice were injected with BM ($2 \times 10^6$/g, ~$50 \times 10^6$/mouse) and $CD4^+$ T-depleted spleen cells ($4 \times 10^6$/g) from C57BL/6 donors. The recipients were monitored for clinical signs of GVHD and checked for chimerism eight weeks after HCT. Zero of the twelve recipients conditioned with anti-CD3 alone developed chimerism, but all twelve of the recipients conditioned with anti-CD3 and SAHA developed complete chimerism wherein almost all T, B, macrophage, and granulocyte cells were donor-type (Table 1 and FIG. 3A). No clinical signs of GVHD were observed in the chimeric recipients, and their body weight change was the same as that of the non-chimeric mice given conditioning only (FIG. 3B). These results indicate that SAHA augments the induction of chimerism without augmenting the induction of GVHD when co-injected with anti-CD3 for conditioning allogeneic recipients.

Next, the mechanisms by which SAHA augments engraftment in anti-CD3-conditioned recipients were tested. Since host T cells play a major role in graft rejection, experiments focused on the effect of SAHA on host T cells. Co-injection of low-dose (40 or 100 µg/g) SAHA did not significantly increase apoptosis of host T cells or reduce the yield of residual live T cells in the spleen of treated mice (FIG. 3C). Since low-concentration SAHA inhibited proliferation of anti-CD3 activated T cells although it did not augment apoptosis of the T cells (FIG. 1), the proliferative capacity of T cells from the BALB/c recipients conditioned with anti-CD3 alone or anti-CD3 and SAHA was compared in response to stimulation by C57BL/6 donor dendritic cells. Proliferation of T cells from the former was two-fold greater than that of the latter (P<0.01, FIG. 3D). The cytotoxic activity of the residual host T cells in recipients conditioned with anti-CD3 alone or anti-CD3 plus SAHA was assessed five days after HCT by injection of spleen cells from naïve donor and host mice. Residual host T cells in anti-CD3-conditioned recipients had stronger cytotoxic activity compared to those in recipients conditioned with anti-CD3 and SAHA, so that the ratio of the residual CD45.1$^+$ donor-type targets versus CFSE-labeled host-type targets in the recipients conditioned with anti-CD3 was two-fold lower than that in the recipients conditioned with anti-CD3 plus SAHA (P<0.01, FIGS. 3E & F). Taken together, augmentation of engraftment by conditioning with low-dose SAHA and anti-CD3 occurs at least in part via inhibition of the rejecting function of the residual host T cells.

Example 5

Effect of Conditioning with Both SAHA and Anti-CD3 on Lupus

Sorted allogeneic stem cells have recently been shown to establish mixed chimerism in sublethally irradiated NZB/W F1 recipients and reverse overt lupus (Smith-Berdan 2007). However, 50% of the chimeric recipients continued to have high levels of serum autoantibodies, and about 30% of the chimeric recipients continued to have proteinuria and eventually died of lupus (Smith-Berdan 2007). This indicates that the pathogenic memory T and B cells continue to exist in the lupus recipients with mixed chimerism and continue to mediate lupus. Therefore, induction of complete chimerism may be required for the cure of lupus.

Figure 4:
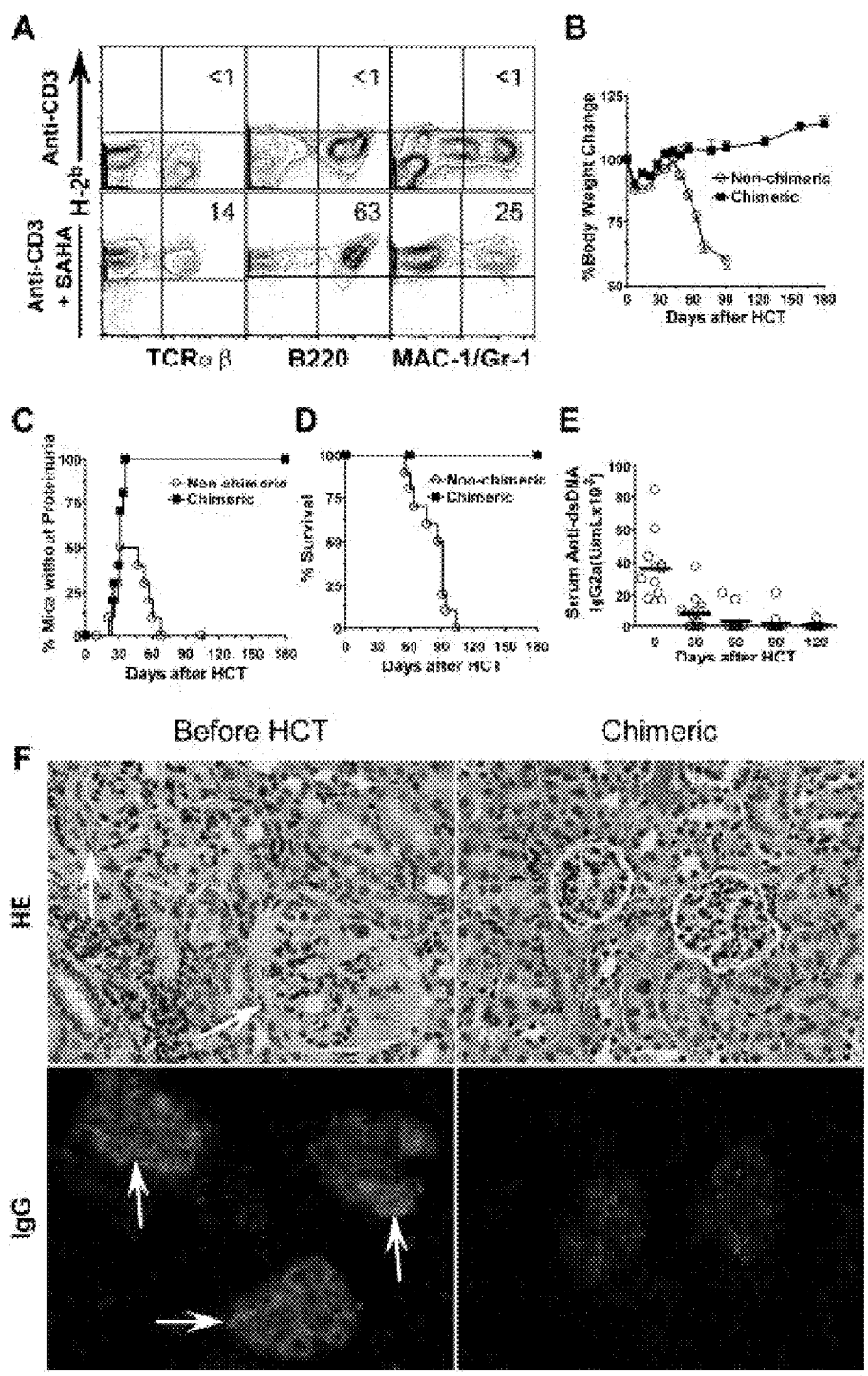
FIG. 4. Old NZB/W F1 mice (>7 months) with severe proteinuria were conditioned with anti-CD3 and SAHA and transplanted with C57BL/6 donor BM ($2 \times 10^6$/g) and CD4+ T-depleted spleen cells ($4 \times 10^6$/g). The recipients were monitored for clinical signs of GVHD daily and body weight and proteinuria twice a week. The recipients were checked for chimerism eight weeks after HCT. A. Blood mononuclear cells of the anti-CD3 and SAHA-conditioned mice with or without HCT were stained for H-2b (donor marker) versus TCRαβ, B220, or Mac-1/Gr-1. The percentage of donor-type T, B, and macrophage cells is shown. One representative of ten mice in each group is shown. B. Body weight change curves of the mice given conditioning alone or conditioning and HCT over a 180-day period after HCT. Mean±SE of ten mice in each group is shown. C and D. Proteinuria change curve and survival curve of the lupus mice given conditioning alone or conditioning and HCT. E. Kinetic changes of serum levels of anti-dsDNA IgG2a antibodies in lupus mice given conditioning and HCT. F. HE staining of kidney tissues and immunofluorescent staining of IgG deposition in glomeruli of the lupus mice before treatment and 180 days after HCT. One representative of four examined mice in each group is shown.

The effect of conditioning with anti-CD3 and SAHA on the induction of complete chimerism without GVHD was assessed in old NZB/W F1 mice with severe glomerulonephritis and proteinuria. One injection of anti-CD3 with multiple injections of low-dose SAHA (40 µg/g) was insufficient for induction of chimerism in old NZB/W F1 mice with severe proteinuria (data not shown). This might be due to the loss of antibody and SAHA in urine, which could have led to the insufficient depletion of host T cells. Therefore, the injections of anti-CD3 and SAHA were repeated five days after the first injection. Five days after the second injection, the mice were infused with the same dose of donor BM cells (2×10$^6$/g) and CD4$^+$ T-depleted spleen cells (4×10$^6$/g) as used for the old BALB/c mice. While none of the ten recipients conditioned with anti-CD3 alone developed chimerism, all ten of the recipients conditioned with anti-CD3 and SAHA developed complete chimerism (Table 1 and FIG. 4A). In addition, the chimeric recipients showed no clinical signs of GVHD over a 180-day period after HCT, and the recipients showed a steady body weight increase as they aged. In contrast, the non-chimeric recipients conditioned with anti-CD3 alone showed severe body weight loss due to the progression of lupus (FIG. 4B).

Proteinuria, serum autoantibody levels, and survival of the lupus mice with or without chimerism were longitudinally monitored. The non-chimeric recipients conditioned with anti-CD3 alone temporarily reversed lupus in about 50% of the mice, but they all showed severe proteinuria again 60 days after treatment and all died 120 days after treatment (FIGS. 4C and D). In contrast, all the chimeric recipients became proteinuria-free around 50 days after HCT and all survived for more than 180 days after HCT (FIGS. 4C and D). The serum anti-dsDNA levels of the chimeric recipients gradually decreased and became almost undetectable by 60 days after HCT (FIG. 4E). The histopathology of the kidneys of the chimeric recipients was compared to that of the lupus mice before HCT. While the glomeruli of the untreated lupus mice appeared swollen and had severe IgG deposition, the glomeruli of the chimeric recipients appeared to be normal and had very little IgG deposition (FIG. 4F). These results indicate that conditioning with anti-CD3 and SAHA allow donor CD8$^+$ T cells to eliminate host memory pathogenic T cells and autoantibody-secreting B cells without causing GVHD and thereby "cure" lupus glomerulonephritis.

Example 6

Effect of Anti-CD3 Preconditioning on GVHD and GVL in TBI-Conditioned Recipients To determine whether anti-CD3 preconditioning could separate GVL from GVHD, recipient BALB/c mice were injected with anti-CD3 (5 µg/g) or PBS as preconditioning. Nine days after anti-CD3 injection, the mice were conditioned with TBI. At this time point, serum anti-CD3 was not detectable by blocking assay and the host TCRαβ$^+$ cells were also not detectable in blood. Six hours after TBI, the recipients were injected i.v. with TCD-BM (5×10$^6$) and spleen cells (2.5–5×10$^6$) from C57BL/6 donor mice. The recipients were monitored daily for clinical GVHD including body weight, posture, diarrhea, and survival.

Injection of 5×10$^6$ TCD-BM induced severe clinical GVHD in control recipients without anti-CD3 preconditioning, and all recipients died by 15 days after HCT. Recipients that were preconditioned with anti-CD3, however, exhibited only moderate GVHD, and 91% (11/12) survived for more than 100 days (P<0.01, FIGS. 5A and B).

Similarly, injections of 2.5×10$^6$ donor spleen cells induced severe GVHD in the control recipients, with only 42% (5/12) surviving for more than 100 days after HCT. In contrast, the same dose of donor cells induced minimum clinical GVHD in anti-CD3-preconditioned recipients and all the recipients survived for more than 100 days (FIGS. 5A and B). Therefore, anti-CD3 preconditioning markedly reduced clinical GVHD.

Other experiments were performed to compare the histopathology of liver, skin, and colon of the recipients with or without anti-CD3 preconditioning 60 days after injection of 2.5×10$^6$ donor spleen cells. Anti-CD3 preconditioning markedly reduced the infiltration and tissue damages in liver, skin, and colon (P<0.01, FIGS. 5C and D). Taken together, these results show that anti-CD3 preconditioning prevents induction of acute GVHD.

Luciferase transfected (Luc⁺) BCL1 leukemia/lymphoma cells ($0.5 \times 10^6$) were co-injected with donor TCD-BM ($5 \times 10^6$) and spleen cells ($2.5 \times 10^6$) into anti-CD3-preconditioned recipients six hours after TBI-conditioning. Control recipients were injected with TCD-BM and Luc⁺ BCL1 cells only. All recipients were monitored for survival daily and for tumor growth using in vivo BLI weekly.

Luc⁺ BCL1 tumor cells grew rapidly in recipients given TCD-BM without donor spleen cells, and killed the recipients 30-40 days after HCT (FIG. 5E-G). In contrast, after a transient growth, Luc⁺ BCL1 tumor cells were eliminated in the recipients transplanted with both TCD-BM and spleen cells, and all the recipients survived for more than 100 days with little clinical GVHD ($P<0.01$, FIG. 5E-G). Consistently, anti-CD3-preconditioning reduced the serum levels of Th1 cytokine IFN-$\gamma$, TNF-$\alpha$ by 2-5 fold ($P<0.01$, FIGS. 6F & G). These results indicate that anti-CD3 preconditioning prevents GVHD but retains GVL activity.

Example 7

Effect of anti-CD3 Preconditioning on Donor Th1 Differentiation and Donor T Cell Infiltration of GVHD Target Tissues It has been reported that donor T cell expansion in TBI-conditioned recipients reached first peak 5 days after HCT (Beilhack 2005, Zhang 2007a). Therefore, the percentage and yield of donor T cells in lymphoid and GVHD target tissues (liver, gut, and skin) were compared in recipients with or without anti-CD3 preconditioning five days after injection of donor TCD-BM and spleen cells ($5 \times 10^6$).

Figure 6:
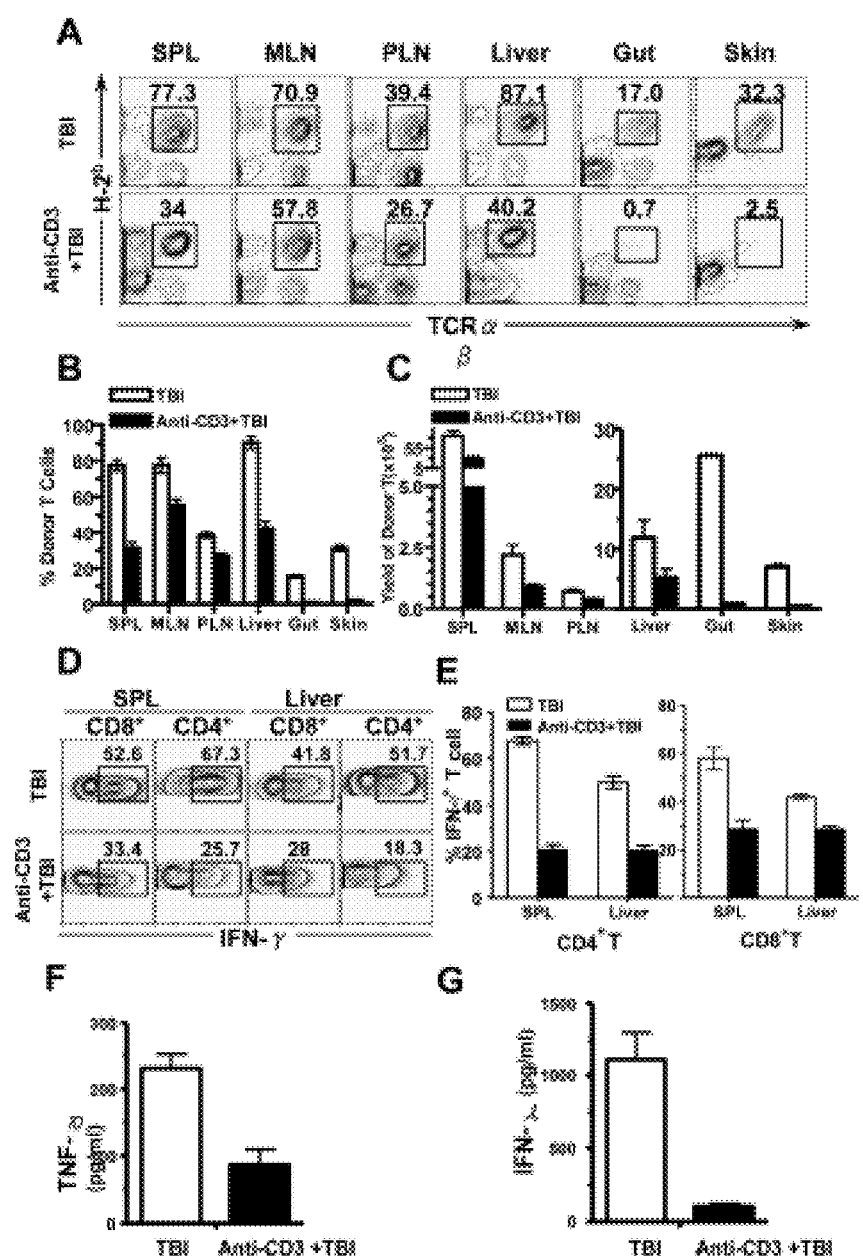
FIG. 6. Anti-CD3 preconditioning inhibited donor T cell infiltration of GVHD target tissues. Five days after injection of donor TCD-BM and spleen cells ($5 \times 10^6$), the percentage and yield of donor T cells in spleen, MLN, PLN, liver, gut and skin of the recipients with or without anti-CD3 preconditioning were compared. There were 4 recipients in each group. A, A representative FACS pattern. Mononuclear cells from different tissues were stained with anti-TCRαβ versus anti-H-2$^b$ (donor MHC I), and the donor-type T cells were gated. B, Mean±SE of the donor T cell percentage among total mononuclear cells of 4 recipients. C, Mean±SE of the yield of donor T cells in different tissues. D, A representative intracellular IFN-γ staining pattern of the gated H-2$^{b+}$ CD4+ or H-2$^{b+}$ CD8+ T cells. The IFN-γ+ cells were gated. E, Mean±SE of the percentage of donor IFN-γ+ CD4+ or CD8+ cells of 4 examined recipients.

The percentage and yield of donor T cells in the spleen, mesenteric lymph node (MLN), and peripheral lymph node (PLN) of the recipients with anti-CD3 preconditioning were about 2-fold lower than that of the control recipients ($P<0.01$, FIG. 6A-C). In contrast, the percentage and yield of donor T cells in the skin and gut of the recipients preconditioned with anti-CD3 was more than 15-fold lower than that of the control recipients ($P<0.01$, FIG. 6A-C). These results indicate that anti-CD3 preconditioning markedly inhibits donor T cell migration into GVHD target tissues such as gut and skin in TBI-conditioned recipients.

Figure 5:
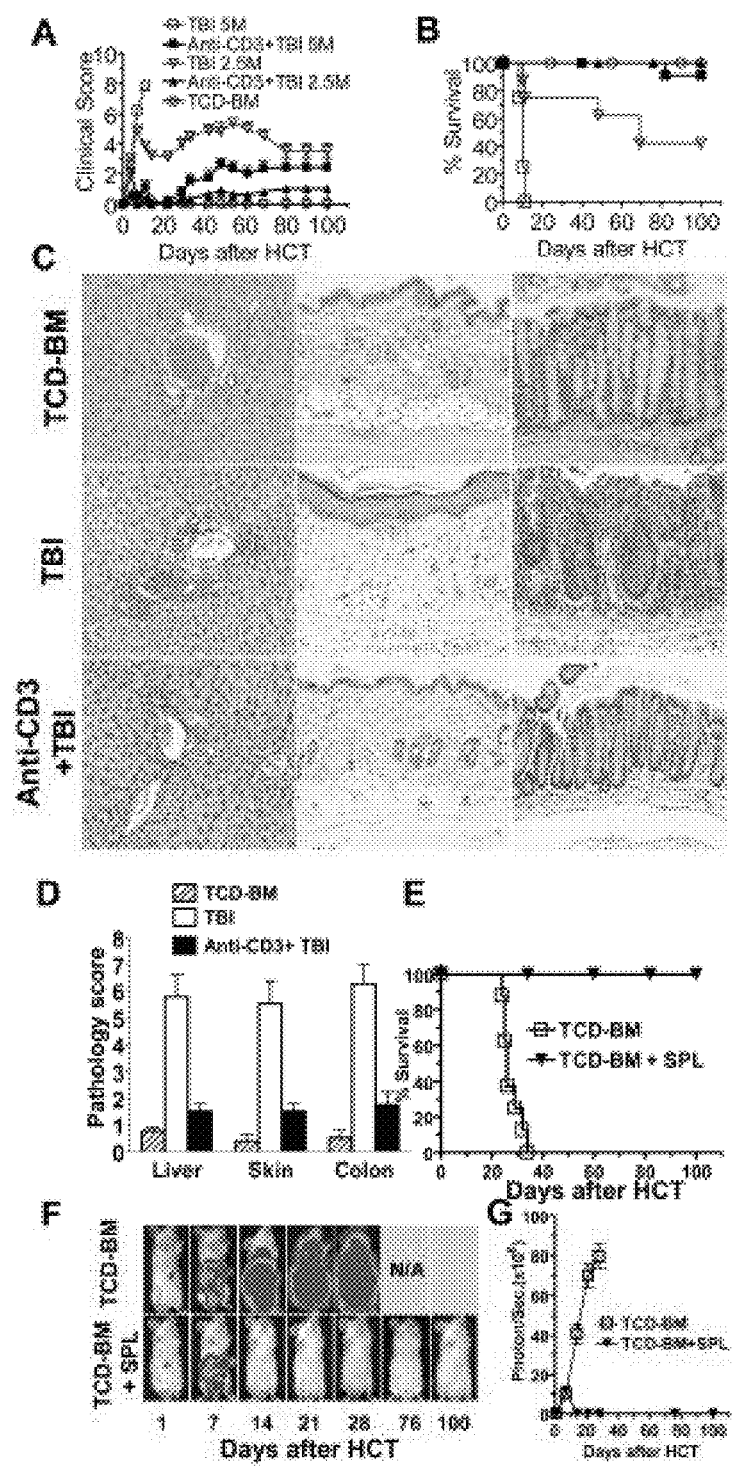
FIG. 5. Anti-CD3 preconditioning separated GVL from GVHD in TBI-conditioned recipients. BALB/c mice were preconditioned with anti-CD3 on Day-9. The mice were conditioned with 800 rads sublethal TBI on Day 0. Six hours later, the mice were injected i.v. with TCD-BM cells ($5 \times 10^6$) and spleen cells (2.5 or $5 \times 10^6$) from C57BL/6 donors. There were 12 mice in each group combined from 3 replicate experiments. A, Clinical score. B, Survival percentage. C and D, with an additional experiment, liver, skin, and colon tissues from the TBI-conditioned recipients with or without anti-CD3 preconditioning were evaluated for tissue inflammation and damage 60 days after HCT. A representative histopathology and the mean±SE of 6 recipients in each group are shown. E-G, Anti-CD3-preconditioned BALB/C recipients were injected i.v. with BCL1 cells transfected with luciferase (Luc+), and donor TCD-BM and spleen cells ($2.5 \times 10^6$). There were 8 mice in each group combined from 2 replicate experiments. The survival percentage, representative photos of in vivo bioluminescent imaging of Luc+ BCL1 cells, and the intensity (photo/second) of BLI are shown.

Interestingly, the percentage and yield of donor T cells in the liver of recipients with anti-CD3 preconditioning was only about 2-fold lower than that of the control recipients, although the difference was significant ($P<0.01$, FIG. 6A-C). These results were markedly different than what was observed in the skin and gut tissues, but similar to spleen (FIG. 6A-C). This may be due to the fact that donor T cells can directly enter spleen and liver by blood circulation. In spite of the moderate difference in donor T cell yield from liver of recipients with or without anti-CD3 preconditioning early after HCT, the clinical acute GVHD of the recipients from the two groups was markedly different (FIG. 5). Because IFN-$\gamma$-producing Th1 and Tc1 cells were reported to play an important role in mediating acute GVHD target tissue damage (Yi 2008, Blazar 2003), the percentage of IFN-$\gamma^+$ donor CD4⁺ and CD8⁺ T cells in spleen and liver of the recipients was compared.

Anti-CD3 preconditioning reduced the percentage of IFN-$\gamma^+$ cells among total CD4⁺ and CD8⁺ T cells by about 2-fold in the spleen and liver as compared to that of the control recipients ($P<0.01$, FIGS. 6D & E). These results indicate that anti-CD3 preconditioning leads to significant reduction of donor Th1 differentiation.

Example 8

Effect of Anti-CD3 Preconditioning on Upregulation of Chemokine Receptors by Donor T Cells and Chemokine Release by GVHD Target Tissues in TBI-Conditioned Recipients It has been reported that homing and chemokine receptors expressed by donor T cells as well as chemokines released by GVHD target tissues play a critical role in donor T cell migration into GVHD target tissues (Sackstein 2006, Wysocki 2005, Chakraverty 2006). It has also been proposed that donor T cell expression of homing and chemokine receptors are induced by host DCs in draining lymph nodes (Sackstein 2006, Kim 2008); homing receptor $\alpha 4\beta 7$ and chemokine receptor CCR9 mediate donor T cell migration into gut (Johansson-Lindbom 2003, Mora 2005); and homing receptor E-selectin and P-selectin ligands and chemokine receptors CCR4 and CCR10 mediate donor T cell migration into skin tissues (Mora 2005, Tietz 1998, Reiss 2001). Therefore, donor T cell expression of homing and chemokine receptors in MLN and PLN of recipients with or without anti-CD3 preconditioning was compared.

Figure 7:
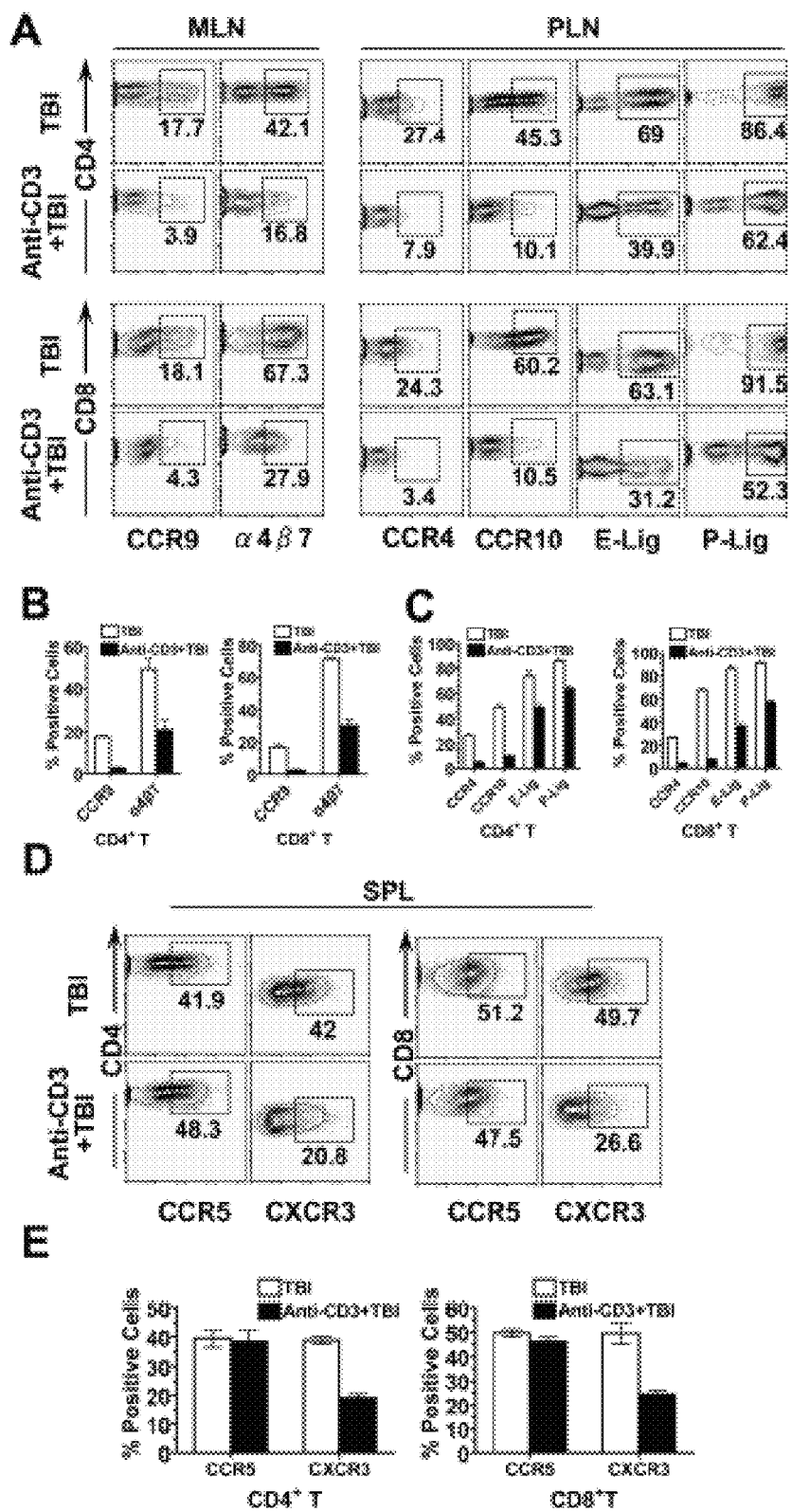
FIG. 7. Anti-CD3 preconditioning inhibited donor T cell expression of homing and chemokine receptors. Five days after HCT, donor T cell expression of gut homing α4β7 and CCR9 receptors in MLN, donor T cell expression of skin homing E-Ligand, P-Ligand, CCR4 and CCR10 in PLN, and donor T expression of non-tissue specific CCR5 and CXCR3 chemokine receptors in spleen were compared. There were 4 recipients in each group. A, A representative FACS pattern of CCR9 and α4β7 by gated H-2b+CD4+ or H-2b+CD8+ donor T cells from MLN, as well as representative FACS pattern of CCR4, CCR10, E-Lig, and P-Lig of donor CD4+ or CD8+ T cells from PLN. B. Mean±SE of CCR9+ or α4β7+ cells among donor CD4+ or CD8+ T cells from MLN. C, Mean±SE of CCR4+, CCR10+, E-Lig+ or P-Lig+ cells among donor CD4+ or CD8+ T cells from PLN. D, A representative FACS pattern of CCR5 and CXCR3 by gated H-2b+CD4+ or H-2b+ CD8+ donor T cells from spleen. E, Mean±SE of CCR5+ or CXCR3+ cells among gated donor CD4+ or CD8+ T cells from spleen of 4 recipients.

Anti-CD3 preconditioning reduced the percentage of $\alpha 4\beta 7^+$, CD4⁺, and CD8⁺ T cells in MLN more than 2-fold, and reduced the percentage of CCR9⁺, CD4⁺, and CD8⁺ T cells more than 4-fold ($P<0.01$, FIGS. 7A and B). Similarly, anti-CD3 preconditioning reduced the percentage of E-Lig⁺ or P-Lig⁺, CD4⁺, and CD8⁺ T cells in PLN by about 2-fold and reduced the percentage of CCR4⁺ or CCR10⁺, CD4⁺, and CD8⁺ T cells by about 5 fold ($P<0.01$, FIGS. 7A & B). These results indicate that anti-CD3 preconditioning inhibit donor T cell upregulation of homing and chemokine receptors in host draining LNs.

It has been reported previously that CCR5 and CXCR3 are expressed by Th1 cells and mediate T cell infiltration of non-specific GVHD target tissues (Wysocki 2004, Duffner 2003, Olson 2002). Therefore, donor T cell expression of CCR5 and CXCR3 in the spleens of recipients with or without anti-CD3 preconditioning were compared.

Although there was no significant difference in the percentage of donor CCR5⁺, CD4⁺, and CD8⁺ T cells, there was a 2-fold reduction in the percentage of CXCR3⁺, CD4⁺, and CD8⁺ T cells in the anti-CD3-preconditioned recipients (FIGS. 7D & E). These results indicate that anti-CD3 preconditioning inhibits donor T expression of some non-tissue specific chemokine receptors.

Figure 8:
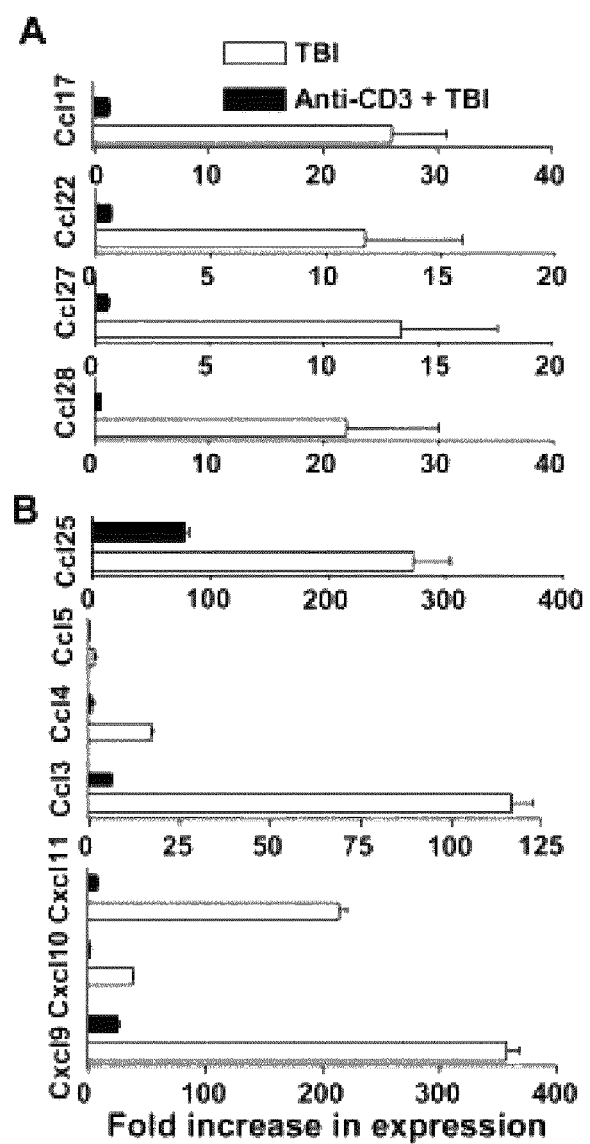
FIG. 8. Anti-CD3 preconditioning inhibited GVHD target tissue expression of chemokines. Expression of chemokine mRNA at day 5 after HCT in various tissues (including skin and colon) of TBI-conditioned recipients with or without anti-CD3 preconditioning was measured by real-time PCR. A, Expression of Ccl17, Ccl22, Ccl27 and Ccl28 by skin tissues. B, Expression of Ccl25, Ccl3-5 and CXCL9-11 by colon tissue. Data were presented relative to the expression in the syngeneic control recipients. Mean±SE of 4 recipients in each group is shown.
Figure 11:
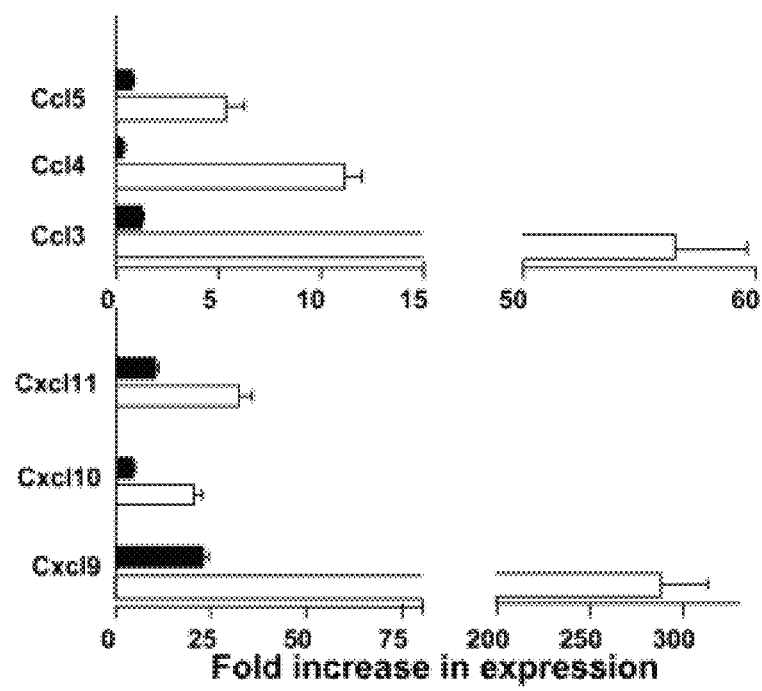
FIG. 11. Anti-CD3 preconditioning inhibited liver tissue expression of chemokines. Five days after HCT, liver tissue expression of Ccl3-5 and Cxcl9-11 was measured with real-time PCR. Mean±SE of 4 replicate experiments is shown.

GVHD target tissue expression of chemokines, including skin tissue expression of CCL17, CCL22 (CCR4 ligand), CCL27, and CCL28 (CCR10 ligand), gut tissue expression of CCL25 (CCR9 ligand), and non-tissue specific chemokines CCL3-5 (CCR5 ligand) and CXCL9-11 (CXCR3 ligand) was analyzed. Anti-CD3 preconditioning reduced skin tissue expression of CCL17, CCL22, CCL27, and CCL28 more than 10-fold, and reduced gut tissue expression of CCL25 more than 3-fold ($P<0.01$, FIG. 8). In addition, anti-CD3 preconditioning reduced gut, skin, and liver tissue expression of CCL3-5 and CXCL9-11 more than 10 fold ($P<0.01$, FIG. 8B, and FIG. 11). These results indicate that anti-CD3 preconditioning inhibits the release of inflammatory chemokines in GVHD target tissues trigged by TBI-conditioning.

Example 9

Effect of Anti-CD3 Preconditioning on Percentage and Yield of CD103⁺ DCs in MLN and MLN DC Capacity for Imprinting Donor T Cell Expression of Gut Homing and Chemokine Receptors A marked reduction of $\alpha 4\beta 7^+$ CCR9⁺ donor T cells in MLN of recipients preconditioned with anti-CD3 was observed (FIG. 7), and it has been reported that CD103+ DCs in MLN induced T cell expression of α4β7 and CCR9 (Johansson-Lindbom 2003). Therefore, the effect of anti-CD3 preconditioning on the percentage and yield of CD103+ DCs in MLN as well as the capacity of MLN DCs in inducing donor T expression of gut homing α4β7 and CCR9 chemokine receptors.

Figure 9:
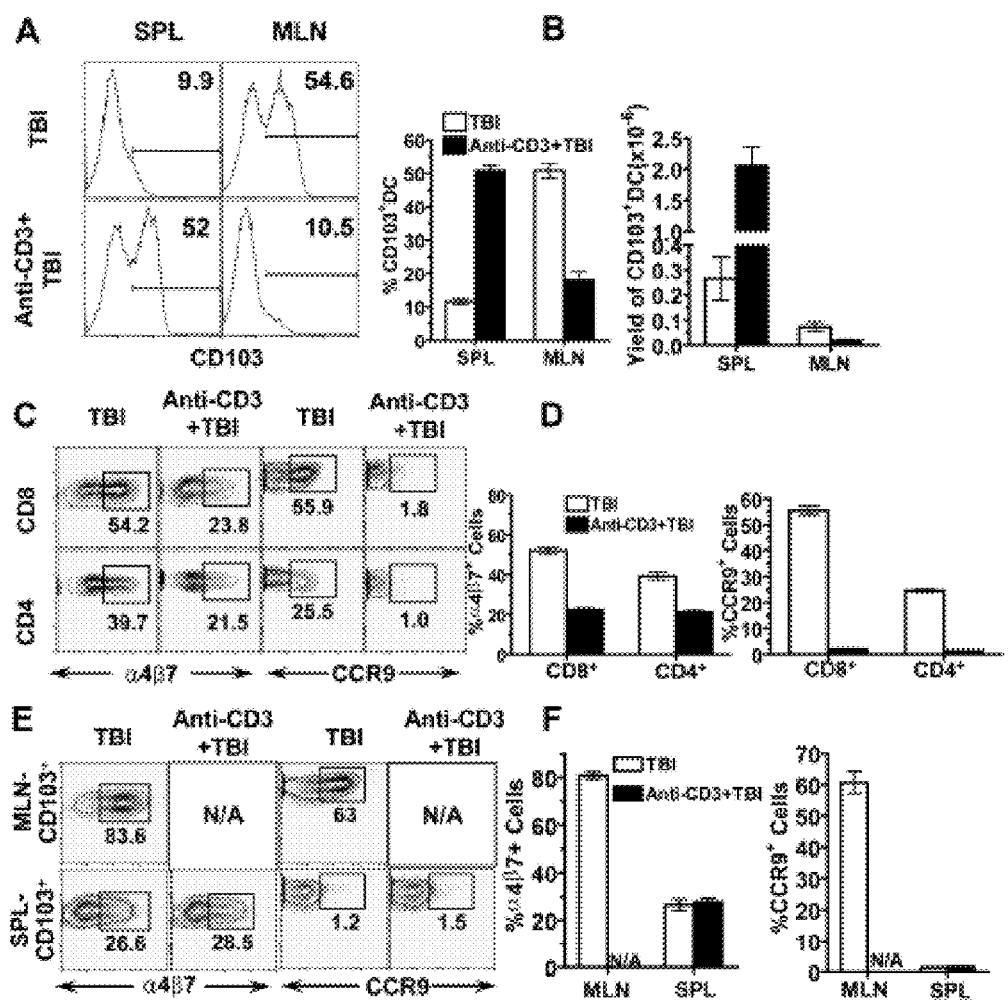
FIG. 9. Anti-CD3 preconditioning reduced CD103+ DCs in MLN and reduced MLN DC capacity in induction of donor T cell expression of α4β7 and CCR9. Spleen and MLN cells of BALB/c mice with or without anti-CD3 preconditioning were harvested and enriched for CD11c+ DCs by micromagnetic beads. The CD11c+ enriched cells were further analyzed with flow cytometry or used for in vitro culture. A, A representative FACS pattern of CD103 expression among CD11c+ DCs. B, Mean±SE of CD103+ cells among CD11c+ DCs and the yield of CD103+ CD11c+ DCs in spleen and MLN of 4 mice with or without anti-CD3 preconditioning. C, Sorted CD4+/CD8+ T cells ($0.2 \times 10^6$) from C57BL/6 spleen were co-cultured with enriched CD11c+ DCs ($0.1 \times 10^6$) from the MLN of host BALB/c mice with or without anti-CD3 preconditioning for 4 days. Thereafter, donor CD4+ or CD8+ T cells were analyzed for the expression of α4β7 and CCR9. One representative of 4 replicate experiments is shown. D, Mean±SE of the percentage of α4β7+ or CCR9+ cells among donor CD4+ or CD8+ T cells in the culture of the 4 experiments. E, Sorted donor CD8+ T cells ($0.2 \times 10^6$) were co-cultured with CD103+ DCs ($0.05 \times 10^6$) from MLN and spleen of the host mice, and then donor CD8+ T cell expression of α4β7 and CCR9 were analyzed. The α4β7+ or CCR9+ CD8+ T cells were gated. One representative of 4 replicate experiments is shown. F, Mean±SE of the α4β7+ or CCR9+ cells among donor CD8+ T cells of the 4 experiments.

Anti-CD3 preconditioning reduced the percentage and yield of CD103+ DCs in MLN by about 5-fold, but increased the percentage and yield of CD103+ DCs in spleen by more than 5-fold (P<0.01, FIGS. 9A & B). These results indicate that anti-CD3 preconditioning reduces CD103+ DCs in MLN.

MLN DC capacity in inducing donor T expression of α4β7 and CCR9 in an in vitro culture was determined as described previously (Johansson-Lindbom 2003). CD11c+ DCs from MLN of BALB/c mice without anti-CD3 preconditioning induced about 50% of donor CD8+ T cells to express α4β7 and CCR9 and induced 40% and 25% of donor CD4+ T cells to express α4β7 and CCR9, respectively. In contrast, anti-CD3 preconditioning reduced the DC's capacity in inducing donor CD4+ and CD8+ T expression of α4β7 by 2-fold and almost completely abrogated the DC's capacity in inducing donor CD4+ and CD8+ T expression of CCR9 (P<0.01, FIGS. 9C and D). These results indicate that marked reduction of CD103+ DCs in MLN after anti-CD3 preconditioning leads to marked reduction of MLN DC's capacity in induction of donor T expression of α4β7 and CCR9 receptors.

Because anti-CD3 preconditioning markedly increased the percentage and yield of CD103+ DCs in spleen (FIGS. 9A and B), the spleen and MLN CD103+ DCs were compared in inducing donor T cell expression of α4β7 and CCR9. Accordingly, CD103+ DCs were sorted from MLN and spleen of control mice or anti-CD3-preconditioned mice. Sorted CD103+ DCs were co-cultured with sorted donor CD8+ T cells. CD103+ DCs from MLN of the control mice without anti-CD3 preconditioning induced more than 80% or 60% of donor CD8+ T cells to express α4β7 or CCR9, respectively. In contrast, CD103+ CD11c+ DCs from the spleen of the same mice induced 3-fold less α4β7+ and 50-fold less CCR9+ donor CD8+ T cells (P<0.01, FIGS. 9E and F). Similarly, CD103+ DCs from spleen of anti-CD3 preconditioned mice failed to induce donor CD8+ T expression of CCR9 (FIGS. 9E & F). These results indicate that CD103+ DCs in MLN but not in spleen can efficiently induce donor T cells to upregulate both α4β7 and CCR9. We should point out that, although MLN DCs have been reported to induce CCR9+FoxP3+ Treg cells when co-cultured with OVA specific transgenic CD4+ T cells (Mucida 2007, Coombes 2007), host MLN DCs induce alloreactive donor CD4+ and CD8+ T cells to express only CCR9 but not FoxP3 (data not shown).

Example 10

Reduction of CD103+ DCs in MLN by Anti-CD3 Preconditioning was Associated with Downregulation of CCR7 on CD103+ DCs It has been proposed that CD103+ DCs migration from LP to MLN is dependent on their expression of CCR7 (Johansson-Lindbom 2003). Therefore, CCR7 expression by CD103+ DCs in LP and MLN with or without anti-CD3 preconditioning was compared.

Figure 10:
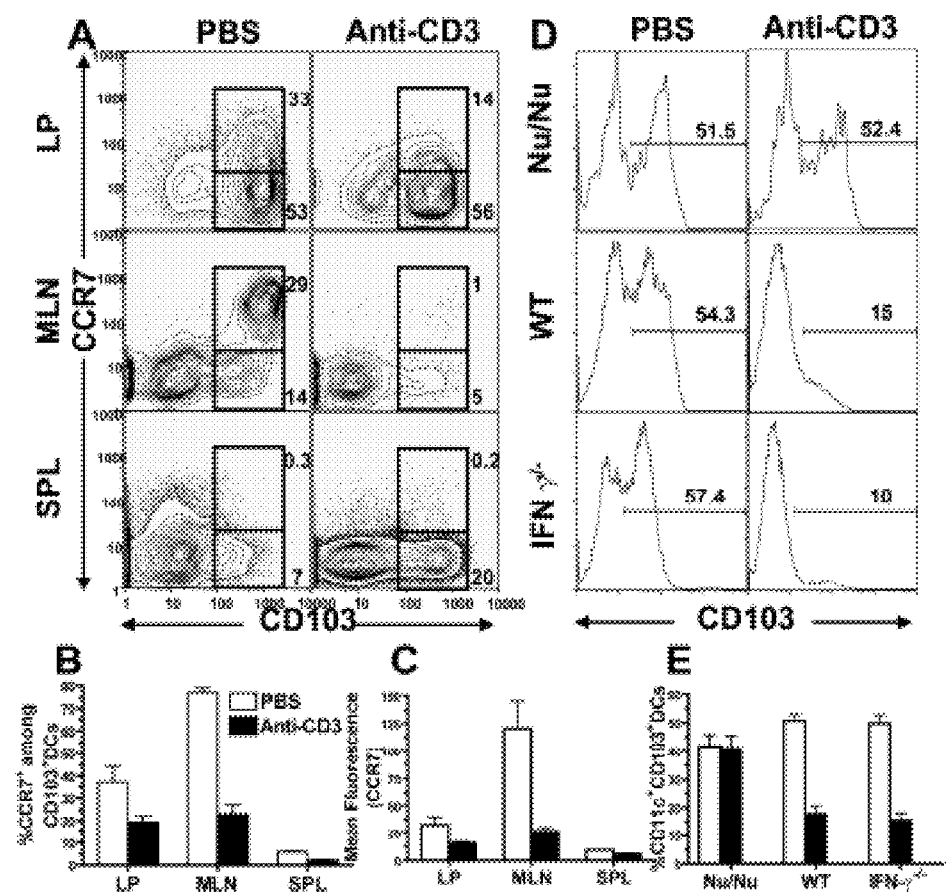
FIG. 10. Anti-CD3 preconditioning downregulated CCR7 expression by CD103+ DCs in intestine LP and MLN, and this effect required anti-CD3 activation of host T cells. A, Nine days after anti-CD3 preconditioning, CD11c+ DCs from LP, MLN and spleen of the BALB/c mice with or without preconditioning were analyzed with flow cytometry. The gated CD11c+ DCs are shown in CD103 versus CCR7. The percentage of CCR7+ CD103+ or CCR7− CD103+ cells among total DCs is shown beside the gating boxes. One representative of 4 replicate experiments is shown. The mean±SE of the percentage of total CD103+ DCs among total CD11c+ DCs in different tissues before and after anti-CD3 preconditioning is 85.4±2.9 versus 72.9±6.5 (LP), 57.2±1.8 versus 8.4±0.8 (MLN), and 7.1±0.8 versus 28.9±3.1 (spleen). B, Mean±SE of CCR7+ cells among CD103+ DCs. C, Mean±SE of CCR7 expression level (mean fluorescence) by CD103+ DCs. D, T cell deficient Nu/Nu mice and IFN-γ$^{-/-}$ mice as well as wild-type mice were preconditioned with anti-CD3 or PBS, 9 days later, the MLN cells were enriched with CD11c+ DCs and the percentage of CD103+ DCs among total CD11c+ DCs was measured. One representative of 4 examined mice in each group is shown. E, Mean±SE of the percentage of CD103+ DCs in MLN of 4 recipients with or without anti-CD3 preconditioning.

Consistent with previous reports (Johansson-Lindbom 2003), most (>85%) of the CD11c+ DCs from LP were CD103+, which was about 2 or 15 fold higher than that in MLN or spleen, respectively (P<0.01, FIG. 10A). CCR7 expression levels on CD103+ DCs in LP were variable, and about 30% of the CD103+ DCs were stained positive for CCR7. Interestingly, the percentage of CCR7+ DCs among CD103+ DCs in MLN was 2-fold higher than that in LP, and their expression levels of CCR7 was 4-fold higher than that in LP (P<0.01, FIG. 10A-C). These results indicate that CD103+ DCs with high-level expression of CCR7 are enriched in MLN.

After anti-CD3 preconditioning, the percentage of CCR7+ CD103+ DCs and their CCR7 expression levels in LP were reduced by more than 2-fold (P<0.01, FIG. 10A-C); accordingly, the percentage of CCR7+CD103+ DCs among total CD11c+ DCs or among residual CD103+ DCs in MLN was reduced by about 30-fold or 4-fold, respectively, and their CCR7 expression levels was reduced by 5-fold (P<0.01, FIG. 10A-C). There was no increase of CCR7+CD103+ DCs in spleen, although the CCR7− CD103+ DCs were increased by 4-fold (P<0.01, FIG. 10A-C). These results indicate that reduction of CD103+ DCs in MLN after anti-CD3 preconditioning is associated with down-regulation of CCR7 expression by CD103+ DCs in LP. This also indicates that anti-CD3 preconditioning may prevent CD103+ DC migration from LP to MLN.

Example 11

Reduction of CD103+ DCs in MLN by Anti-CD3 Preconditioning Required Activation of Host T Cells To test whether anti-CD3 activation of host T cells was necessary for reduction of CD103+ DCs in MLN, the percentage of CD103+ DCs in MLN of wild-type BALB/c and T cell-deficient BALB/c nu/nu mice before and after anti-CD3 preconditioning was compared.

While anti-CD3 preconditioning always markedly reduced the percentage of CD103+ DCs in MLN of wild-type mice, it resulted in little change in BALB/c nu/nu mice (FIGS. 10D and E). These results indicate that anti-CD3-activation of host T cells is required for reduction of CD103+ DCs in MLN.

Because reduction of CD103+ DCs in MLN after anti-CD3 preconditioning was associated with downregulation of CCR7 expression by the CD103+ DCs (FIG. 10A-C), and anti-CD3 preconditioning led to an elevation of serum IFN-γ (Li 2008), a cytokine that was reported to regulate chemokine receptor expression (Olson 2002), CD103+ DC percentage in MLN of IFN-γ−/− mice with or without anti-CD3 preconditioning was compared.

Anti-CD3 preconditioning still markedly reduced the percentage of CD103+ DCs in MLN of IFN-γ−/− mice (P<0.01, FIGS. 10D & E). These results indicate that IFN-γ is not required for reduction of CD103+ DCs in MLN by anti-CD3 preconditioning.

As stated above, the foregoing are merely intended to illustrate the various embodiments of the present invention. As such, the specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

TABLE 1

| Recipient | Conditioning | % chimerism |
| --- | --- | --- |
| Old BALB/c | Anti-CD3 | 0/12 |
|  | Anti-CD3 + SAHA | 12/12 |
| Lupus NZBW F1 | Anti-CD3 | 0/10 |
|  | Anti-CD3 + SAHA | 10/10 |

REFERENCES

1. Alegre, M., et al. 1990. Eur J Immunol 20:707-10.
2. Beaty, S. R., et al. 2007. J Immunol. 178:1882-95.
3. Beilhack, A., et al., 2005. Blood 106:1113-22.
4. Blazar, B. R., et al. 2003. J Immunol 171:1272-77.
5. Chakraverty, R., et al. 2006. J Exp Med 203:2021-31.
6 Chakraverty, R., et al. 2007. Blood 110:9-17.
7. Cooke, K. R., et al. 1996. Blood 88:3230-39.
8. Decalf, J., et al. 2007. J Exp Med 204:2423-2437.
9. Drakes, M. L., et al. 2004. Cytotechnology. 46:151-161.
10. Ferrara, J. & Antin, J. 2004. In *Thomas' Hematopoietic cell transplantation*, ed. Blume, K. G., Forman, S. J., and Appelbaum, F. R. (Blackwell Publishing Ltd, Malden, Mass.), pp. 353-368.
11. Hieshima, K., et al., 2004. J Immunol. 173:3668-75.
12. Kaplan, D. H., et al., 2004. J. Immunol. 173:5467-75.
13. Kim, Y. M., et al. 2003. J Clin Invest 111:659-669.
14. Leng, C., et al. 2006. Exp Hematol 34:776-87.
15. Leoni, F., et al. 2002. Proc Natl Acad Sci USA 99:2995-3000.
16. Liang, Y., et al. 2005. Blood 105:2180-8.
17. Mapara, M. Y., et al. 2006. Biol Blood Marrow Transplant 12:623-634.
18. Marks, P., et al. 2001. Nat Rev Cancer 1:194-202.
19. Marks, P. A., et al. 2003. Curr Opin Pharmacol 3:344-51.
20. Mishra, N., et al. 2003. J Clin Invest 111:539-52.
21. Morris, E. S., et al. 2005. J Clin Invest 115: 3093-103.
22. Murai, M., et al. 1999. J Clin Invest. 104:49-57.
23. Panoskaltsis-Mortari, A., et al. 2004. Blood 103:3590-3598.
24. Reddy, P., et al. 2004. Proc Natl Acad Sci USA 101:3921-6.
25. Reddy, P., et al. 2005. Nat Med 11:1244-1249.
26. Roth, S. Y., et al. 2001. Annu Rev Biochem 70:81-120.
27. Sackstein, R., 2006. Biol Blood Marrow Transplant. 12:2-8.
28. Shizuru, J. 2004. In *Thomas' Hematopoietic cell transplantation*, ed. Blume, K. G., Forman, S. J., and Appelbaum, F. R. (Blackwell Publishing Ltd, Malden, Mass.), pp. 324-343.
29. Shlomchik, W. D., et al. 1999. Science 285:412-5.
30. Shlomchik, W. D., et al. 2007. Nat Rev Immunol 7:340-352.
31. Smith-Berdan, S., et al. 2007. Blood 110:1370-8.
32. Stenstad, H., et al., 2007. Proc Natl Acad Sci USA., 104:10122-27.
33. Sullivan, K. M. 2004. In *Thomas' Hematopoietic cell transplantation*, ed. Blume, K. G., Forman, S. J., and Appelbaum, F. R. (Blackwell Publishing Ltd, Malden, Mass.), pp. 635-664.
34. Sykes, M. & Nikolic, B. 2005. Nature 435:620-7.
35. Teshima, T., et al. 2002. Nat Med 8:575-81.
36. Wekerle, T., et al. 2000. Nat Med 6:464-9.
37. Welniak, L. A., et al. 2007. Annu Rev Immunol 25:139-170.
38. Wysocki, C. A., et al. 2005. Blood 105:4191-99.
39. Xu, W. S., et al. 2007. Oncogene 26:5541-52.
40. Yi, T., et al. 2008. Blood 112:2101-10.
41. Zeng, D., et al. 2000. J Immunol 164:5000-4.
42. Zeng, D, et al. 2002. Blood 99:1449-57.
43. Zeng, D., et al. 2003. J Clin Invest 112:1211-22.
44. Zhang, Y., et al. 2002. J Immunol 169:7111-7118.
45. Zhang, C., et al. 2007a. J Immunol 178:838-50.
46. Zhang, C., et al. 2007b. Proc Natl Acad Sci USA 104: 2337-42.

What is claimed is:

1. A method of conditioning a recipient for hematopoietic cell transplantation consisting essentially of administering a) a therapeutically effective amount of one or more anti-CD3 antibodies sufficient to induce sustained host T cell depletion and b) a therapeutically effective amount of suberoylanilide hydroxamic acid.

2. A method of generating chimerism in a subject consisting essentially of:
  a) administering a therapeutically effective amount of one or more anti-CD3 antibodies sufficient to induce sustained host T cell depletion;
  b) administering a therapeutically effective amount of suberoylanilide hydroxamic acid; and
  c) performing hematopoietic cell transplantation on said subject.

3. The method of claim 2, wherein said one or more anti-CD3 antibodies and said suberoylanilide hydroxamic acid are administered simultaneously.

* * * * *